US008501157B2

(12) United States Patent
Hu et al.

(10) Patent No.: US 8,501,157 B2
(45) Date of Patent: Aug. 6, 2013

(54) HUMANIZED ANTI-VENEZUELAN EQUINE ENCEPHALITIS VIRUS RECOMBINANT ANTIBODIES

(75) Inventors: Wei-Gang Hu, Medicine Hat (CA); Leslie P. Nagata, Medicine Hat (CA)

(73) Assignee: Her Majesty the Queen in right of Canada as represented by The Ministry of National Defence, Ottawa (CA)

( * ) Notice: Subject to any disclaimer, the term of this patent is extended or adjusted under 35 U.S.C. 154(b) by 233 days.

(21) Appl. No.: 12/740,826

(22) PCT Filed: Nov. 3, 2008

(86) PCT No.: PCT/CA2008/001940
§ 371 (c)(1),
(2), (4) Date: Jun. 15, 2010

(87) PCT Pub. No.: WO2009/055936
PCT Pub. Date: May 7, 2009

(65) Prior Publication Data
US 2010/0247532 A1    Sep. 30, 2010

Related U.S. Application Data

(63) Continuation-in-part of application No. 11/933,948, filed on Nov. 1, 2007, now abandoned.

(30) Foreign Application Priority Data

Nov. 1, 2007   (CA) .................................... 2607771

(51) Int. Cl.
| A61K 49/00 | (2006.01) |
| A61K 39/395 | (2006.01) |
| A61K 39/00 | (2006.01) |
| A61K 39/42 | (2006.01) |
| A61K 39/193 | (2006.01) |
| C12Q 1/70 | (2006.01) |

(52) U.S. Cl.
USPC ... 424/9.2; 424/130.1; 424/133.1; 424/147.1; 424/218.1; 435/5

(58) Field of Classification Search
None
See application file for complete search history.

(56) References Cited

U.S. PATENT DOCUMENTS

| 5,968,548 | A | 10/1999 | Wong et al. |
| 6,544,958 | B2 | 4/2003 | Wong et al. |
| 6,800,289 | B2 | 10/2004 | Nagata et al. |
| 6,812,329 | B2 | 11/2004 | Nagata |
| 6,818,748 | B2* | 11/2004 | Fulton et al. ............... 530/387.3 |
| 7,622,111 | B2 | 11/2009 | Nagata et al. |
| 2004/0005333 | A1 | 1/2004 | Nagata et al. |
| 2005/0003482 | A1* | 1/2005 | Fang et al. .................. 435/69.1 |
| 2006/0024666 | A1 | 2/2006 | Frederickson et al. |
| 2009/0117105 | A1 | 5/2009 | Hu et al. |

FOREIGN PATENT DOCUMENTS

| CA | 2458824 | 8/2004 |
| CA | 2462343 | 9/2004 |
| CA | 2607771 | 5/2009 |

OTHER PUBLICATIONS

Weaver SC, Ferro C, Barrera R, Boshell J, Navarro JC. Venezuelan equine encephalitis. Annu Rev Entomol 2004;49:141-74.
Rivas F, Diaz LA, Cardenas VM, Daza E, Bruzon L, Alcala A, et al. Epidemic Venezuelan equine encephalitis in La Guajira, Colombia, 1995. J Infect Dis 1997;175:828-32.
Pittman PR, Makuch RS, Mangiafico JA, Cannon TL, Gibbs PH, Peters CJ. Long-term duration of detectable neutralizing antibodies after administration of live-attenuated VEE vaccine and following booster vaccination with inactivated VEE vaccine. Vaccine 1996; 14:337-43.
Jahrling PB, Stephenson EH. Protective efficacies of live attenuated and formaldehyde-inactivated Venezuelan equine encephalitis virus vaccines against aerosol challenge in hamsters. J Clin Microbiol 1984; 19:429-31.
France JK, Wyrick BC, Trent DW. Biochemical and antigenic comparison of the envelope glycoproteins of Venezuelan equine encephalomyelitis virus strains. J Gen Virol 1979; 44:725-40.
Roehrig JT, Day JW, Kinney RM. Antigenic analysis of the surface glycoproteins of a Venezuelan equine encephalomyelitis virus (TC-83) using monoclonal antibodies. Virology 1982;118:269-78.
Roehrig JT, Mathews JH. The neutralization site on the E2 glycoprotein of Venezuelan equine encephalomyelitis (TC-83) virus is composed of multiple conformationally stable epitopes. Virology 1985; 142:347-56.
Schroff RW, Foon KA, Beatty SM, Oldham RK, Morgan Jr AC. Human anti-murine immunoglobulin responses in patients receiving monoclonal antibody therapy. Cancer Res 1985; 45:879-85.
Verhoeyen M, Milstein C, Winter G. Reshaping human antibodies: grafting an antilysozyme activity. Science 1988; 239:1534-6.
Dall'Acqua WF, Damschroder MM, Zhang J, Woods RM, Widjaja L, Yu J, et al. Antibody humanization by framework shuffling. Methods 2005; 36:43-60.
Hu WG, Alvi AZ, Fulton RE, Suresh MR, Nagata LE. Genetic engineering of streptavidin-binding peptide tagged single-chain variable fragment antibody to Venezuelan equine encephalitis virus. Hybrid Hybridomics 2002; 21:415-20.
Hwang WY, Almagro JC, Buss TN, Tan P, Foote J. Use of human germline genes in a CDR homology-based approach to antibody humanization. Methods 2005; 36:35-42.
van den Ouweland AM, van Duijnhoven HL, Keizer GD, Dorssers LC, Van de Ven WJ. Structural homology between the human fur gene product and the subtilisin-like protease encoded by yeast KEX2. Nucleic Acids Res 1990; 18:664.

(Continued)

Primary Examiner — Benjamin P Blumel
(74) Attorney, Agent, or Firm — Santosh K. Chari; Blake, Cassels & Graydon LLP

(57) ABSTRACT

A CDR grafted humanized recombinant antibody against infection from Venezuelan equine encephalitis virus (VEEV) comprises a human Ig framework having CDRs from murine mAb 1A4A1 VH and VL. DNA sequences, expression vectors incorporating such sequences and transformed host cells are also provided. Also provided are pharmaceutical compositions and methods of prophylaxis and treatment against VEEV infection using the humanized recombinant antibodies of the invention.

10 Claims, 15 Drawing Sheets

OTHER PUBLICATIONS

Johnson KM, Martin DH. Venezuelan equine encephalitis. Adv. Vet Sci Comp Med. 1974; 18(0):79-116.

Groot H, (1972) The health and economic importance of Venezuelan equine encephalitis (VEE) in Venezuelan encephalitis, Scientific publication No. 243, pp. 7-16, Pan American Health Organization, Washington DC.

Phillpotts RJ, Jones LD, Howard SC, Monoclonal antibody protects mice against infection and disease when given either before or up to 24h after airborne challenge with virulent Venezuelan equine encephalitis virus. Vaccine, Feb. 22, 2002; 20 (11-12): 1497-504.

Brekke Ole Henrik; Sandlie Inger; Therapeutic Antibodies for Human Diseases at the Dawn of the Twenty-First Century, 2002 Nature Publishing Group, Jan. 2003, vol. 2, pp. 52-62.

Hu WG, Chau D, Wu J, Jager S, Nagata L, Humanization and mammalian expression of murine monoclonal antibody against Venezuelan equine encephalitis virus. Vaccine, 2007; 25:3210-3214.

Fang J, Qian J, Yi S, Harding T, Tu G, VanRoey M, Jooss K, Stable antibody expression at therapeutic levels using the 2A peptide. Nature Biotechnology, May 2005; vol. 23, No. 5, pp. 584-590.

International Search Report issued in PCT/CA2008/001940 filed on Nov. 3, 2008.

Hunt et al., A humanized murine monoclonal antibody protects mice either before or after challenge with virulent Benezuelan equine encephalomyelitis virus, 2006, Journal of General Virology, vol. 87, pp. 2467-2476.

Genbank Accession # AF170096, *Homo sapiens* isolate MCL-BV/175 immunoglobulin heavy chain VDJ, 2001.

Genbank Accession # DQ322999, *Homo sapiens* immunoglobulin light chain variable region, 2006.

Genbank Accession # AAD55997, immunoglobulin heavy chain VDJ region [*Homo sapiens*], 2001.

Genbank Accession # ABC67121, immunoglobulin light chain variable region YV3-14-K1-34 [*Homo sapiens*], 2006.

Genbank Accession # AAH14258, human immunoglobulin heavy chain, 2006.

Genbank Accession # AAH73763, human immunoglobulin kappa chain, 2005.

O'Brien LM, Underwood-Fowler CD, Goodchild SA, Phelps AL, Phillpotts RJ. Development of a novel monoclonal antibody with reactivity to a wide range of Venezuelan equine encephalitis virus strains. Virol J. Nov. 19, 2009; 6:206.

Kirsch MI. Holseweh B. Nacke C. Rulker T, Schirmann T, Marschall HJ, Hust M. Dübel S.—Development of human antibody fragments using antibody phage display for the detection and diagnosis of Venezuelan equine encephalitis virus (VEEV). BMC Biotechnol. Sep. 2, 2008; 8:66.

Hu WG, Chau D, Wu J, Jager S. Nagata LP—Humanization and mammalian expression of a murine monoclonal antibody against Venezuelan equine encephalitis virus. Vaccine. Apr. 20, 2007;25(16):3210-4.

Hunt AR, Frederickson S. Hinkel C. Bowdish KS, Roehrig JT—A humanized murine monoclonal antibody protects mice either before or after challenge with virulent Venezuelan equine encephalomyelitis virus. J Gen Virol. Sep. 2006; 87(Pt 9) 2467-76.

Phillpotts RJ—Venezuelan equine encephalitis virus complex-specific monoclonal antibody provides broad protection, in murine models, against airborne challenge with viruses from serogroups I, II, and III. Virus Res. Sep. 2006; 120(1-2):107-12.

Hu, WG, Alvi AZ, Chau D, Coles JE, Fulton RE, Suresh MR, Nagata LP.—Development and characterization of a novel fusion protein composed of a human IgG1 heavy chain constant region and a single-chain fragment variable antibody against Venezuelan equine encephalitis virus. J Biochem. Jan. 2003; 133(1):59-66.

Alvi AZ, Hu WG, Fulton ER, Coles JF, Long MC, Nagata LP.—Functional enhancement of a partially active single chain variable fragment antibody to Venezuelan equine encephalitis virus. Viral Immunology. 2003; 16(2): 213-222.

Phillpotts RJ, Jones LD, Howard SC.—Monoclonal antibody protects mice against infection and disease when given either before or up to 24 h after airborne challenge with virulent Venezuelan equine encephalitis virus. Vaccine. Feb. 22, 2002;20(11-12):1497-504.

\* cited by examiner

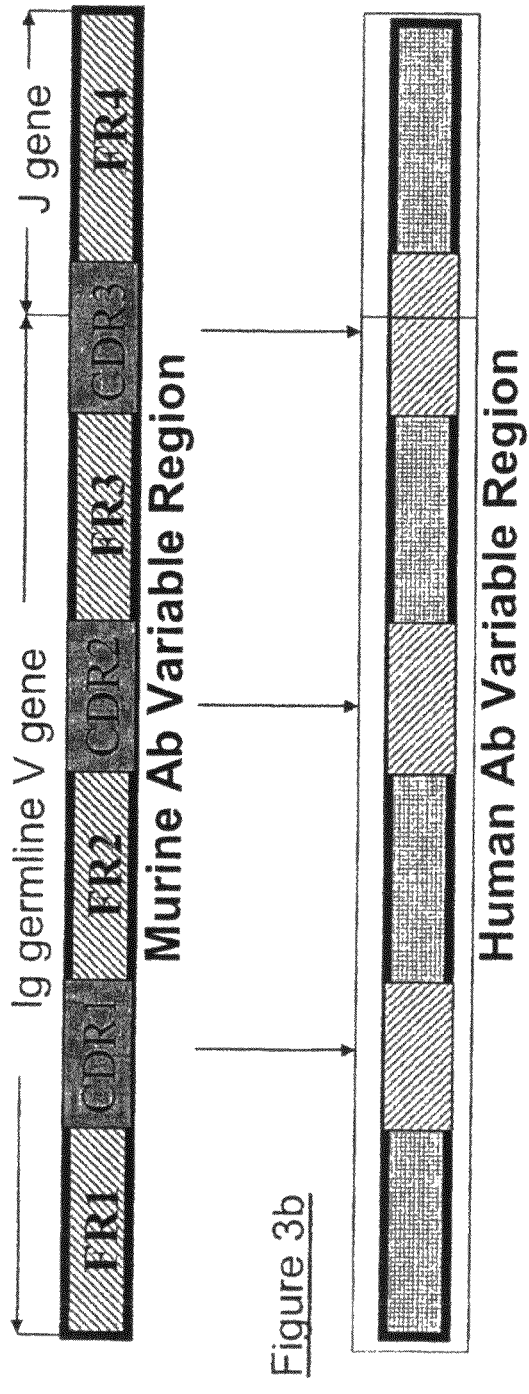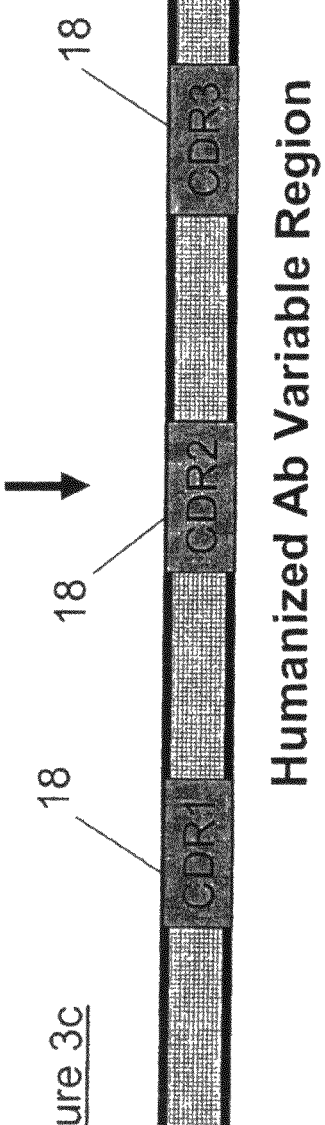
Figure 3a
Figure 3b
Figure 3c

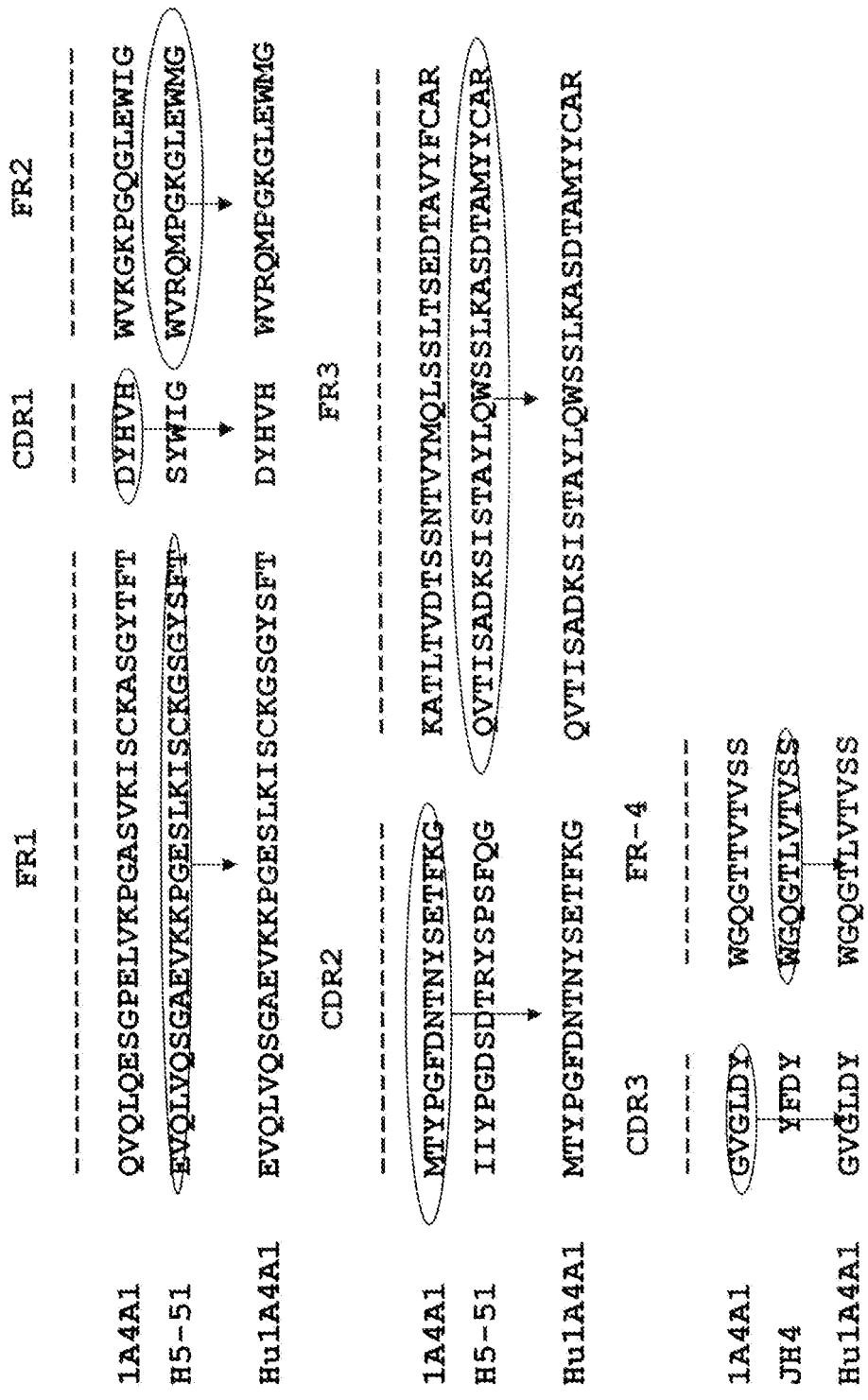

Figure 6

| | FR1 | CDR1 | FR2 |
|---|---|---|---|
| 1A4A1 | DIELTQSPNSLSTSIGDRIRITC | KASQDVDTAVG | WYQQRPGQSPKLLIF |
| L15 | DIQMTQSPSSLSASVGDRVTITC | RASQGISSWLA | WYQQKPEKAPKSLIY |
| HuA4A1 | DIQMTQSPSSLSASVGDRVTITC | KASQDVDTAVG | WYQQKPEKAPKSLIY |

| | CDR2 | FR3 | CDR3 |
|---|---|---|---|
| 1A4A1 | WSSTRHT | GVPDRFTGSGSGTDFTLTISNVQSEDLADYFC | HQYSSYPFT |
| L15 | AASSLQS | GVPSRFSGSGSGTDFTLTISSLQPEDFATYYC | QQYNSYP |
| JK3 | | | FT |
| HuA4A1 | WSSTRHT | GVPSRFSGSGSGTDFTLTISSLQPEDFATYYC | HQYSSYPFT |

| | FR4 |
|---|---|
| 1A4A1 | FGSGTKLEIKR |
| JK3 | FGPGTKVDIKR |
| HuA4A1 | FGPGTKVDIKR |

SEQUENCE LISTING

<160> NUMBER OF SEQ ID NOS: 14

<210> SEQ ID NO 1
<211> LENGTH: 5
<212> TYPE: PRT
<213> ORGANISM: mouse

```
<400> SEQUENCE: 1

Asp Tyr His Val His
1               5

<210> SEQ ID NO 2
<211> LENGTH: 17
<212> TYPE: PRT
<213> ORGANISM: mouse

<400> SEQUENCE: 2

Met Thr Tyr Pro Gly Phe Asp Asn Thr Asn Tyr Ser Glu Thr Phe Lys
1               5                   10                  15

Gly

<210> SEQ ID NO 3
<211> LENGTH: 6
<212> TYPE: PRT
<213> ORGANISM: mouse

<400> SEQUENCE: 3

Gly Val Gly Leu Asp Tyr
1               5

<210> SEQ ID NO 4
<211> LENGTH: 11
<212> TYPE: PRT
<213> ORGANISM: mouse

<400> SEQUENCE: 4

Lys Ala Ser Gln Asp Val Asp Thr Ala Val Gly
1               5                   10

<210> SEQ ID NO 5
<211> LENGTH: 7
<212> TYPE: PRT
<213> ORGANISM: mouse

<400> SEQUENCE: 5

Trp Ser Ser Thr Arg His Thr
1               5

<210> SEQ ID NO 6
<211> LENGTH: 9
<212> TYPE: PRT
<213> ORGANISM: mouse

<400> SEQUENCE: 6

His Gln Tyr Ser Ser Tyr Pro Phe Thr
1               5

<210> SEQ ID NO 7
<211> LENGTH: 115
<212> TYPE: PRT
<213> ORGANISM: Artificial
<220> FEATURE:
<223> OTHER INFORMATION: Humanized VH region with grafted 1A4A1 CDRs

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

His Val His Trp Val Arg Gln Met Pro Gly Lys Gly Leu Glu Trp Met
            35                  40                  45
```

Gly Met Thr Tyr Pro Gly Phe Asp Asn Thr Asn Tyr Ser Glu Thr Phe
        50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Gly Val Gly Leu Asp Tyr Trp Gly Gln Gly Thr Leu Val Thr
            100                 105                 110

Val Ser Ser
        115

<210> SEQ ID NO 8
<211> LENGTH: 108
<212> TYPE: PRT
<213> ORGANISM: Artificial
<220> FEATURE:
<223> OTHER INFORMATION: Humanized VL region with grafted 1A4A1 CDRs

<400> SEQUENCE: 8

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Asp Thr Ala
                20                  25                  30

Val Gly Trp Tyr Gln Gln Lys Pro Glu Lys Ala Pro Lys Ser Leu Ile
             35                  40                  45

Tyr Trp Ser Ser Thr Arg His Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Tyr Ser Ser Tyr Pro Phe
                85                  90                  95

Thr Phe Gly Pro Gly Thr Lys Val Asp Ile Lys Arg
            100                 105

<210> SEQ ID NO 9
<211> LENGTH: 6
<212> TYPE: PRT
<213> ORGANISM: Artificial
<220> FEATURE:
<223> OTHER INFORMATION: Furin recognition site (furin linker)

<400> SEQUENCE: 9

Arg Gly Arg Lys Arg Arg
 1               5

<210> SEQ ID NO 10
<211> LENGTH: 24
<212> TYPE: PRT
<213> ORGANISM: Artificial
<220> FEATURE:
<223> OTHER INFORMATION: FMDV self processing sequence (2A linker)

<400> SEQUENCE: 10

Ala Pro Val Lys Gln Thr Leu Asn Phe Asp Leu Leu Lys Leu Ala Gly
 1               5                  10                  15

Asp Val Glu Ser Asn Pro Gly Pro
            20

<210> SEQ ID NO 11
<211> LENGTH: 2070
<212> TYPE: DNA

<213> ORGANISM: Artificial
<220> FEATURE:
<223> OTHER INFORMATION: Hu1A4A1IgG1-Furin DNA Sequence

<400> SEQUENCE: 11

```
atggacatga gggtcctcgc tcagctcctg gggctcctgc tgctctgttt cccaggtgcc    60
agatgtgata tccagatgac ccagtctcca tcctcactgt ctgcatctgt aggagacaga   120
gtcaccatca cttgtaaggc cagccaggac gtggacaccg ccgtgggctg gtatcagcag   180
aaaccagaga agcccctaa gtccctgatc tattggagca gcacccggca caccggggtc   240
ccatcaaggt tcagcggcag tggatctggg acagatttca ctctcaccat cagcagcctg   300
cagcctgaag attttgcaac ttattactgc caccagtaca gcagctaccc cttcaccttc   360
ggccctggga ccaaagtgga catcaaacgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgttc tggtcgtgga   720
cgtaagagaa gagaggtgca actagtgcag tctggagcag aggtgaaaaa gcccggggag   780
tctctgaaga tctcctgtaa gggttctgga tacagcttta ccgactacca tgtgcactgg   840
gtgcgccaga tgcccgggaa aggcctggag tggatgggga tgacctaccc cggcttcgac   900
aacaccaact acagcgagac cttcaagggc caggtcacca tctcagccga caagtccatc   960
agcaccgcct acctgcagtg gagcagcctg aaggcctcgg acaccgccat gtattactgt  1020
gcgagaggcg tgggcctgga ctactgggc caaggaaccc tggtcaccgt ctcctcagct  1080
agcaccaagg gcccatcggt cttccccctg gcaccctcct ccaagagcac ctctgggggc  1140
acagcggccc tgggctgcct ggtcaaggac tacttccccg aaccggtgac ggtgtcgtgg  1200
aactcaggcg ccctgaccag cggcgtgcac accttcccgg ctgtcctaca gtcctcagga  1260
ctctactccc tcagcagcgt ggtgaccgtg ccctccagca gcttgggcac ccagacctac  1320
atctgcaacg tgaatcacaa gcccagcaac accaaggtgg acaagaaagt tgagcccaaa  1380
tcttgtgaca aaactcacac gtgcccaccg tgcccagcac ctgaactcct ggggggaccg  1440
tcagtcttcc tcttccccc aaaacccaag gacaccctca tgatctcccg gacccctgag  1500
gtcacatgcg tggtggtgga cgtgagccac gaagaccctg aggtcaagtt caactggtac  1560
gtggacggcg tggaggtgca taatgccaag acaaagccgc gggaggagca gtacaacagc  1620
acgtaccggg tggtcagcgt cctcaccgtc ctgcaccagg actggctgaa tggcaaggag  1680
tacaagtgca aggtctccaa caaagccctc ccagccccca tcgagaaaac catctccaaa  1740
gccaaagggc agccccgaga accacaggtg tacaccctgc ccccatcccg ggatgagctg  1800
accaagaacc aggtcagcct gacctgcctg gtcaaaggct tctatcccag cgacatcgcc  1860
gtggagtggg agagcaatgg gcagccggag aacaactaca agaccacgcc tcccgtgctg  1920
gactccgacg gctccttctt cctctacagc aagctcaccg tggacaagag caggtggcag  1980
caggggaacg tcttctcatg ctccgtgatg catgaggctc tgcacaacca ctacacgcag  2040
aagagcctct ccctgtctcc gggtaaatga                                   2070
```

<210> SEQ ID NO 12
<211> LENGTH: 689
<212> TYPE: PRT

<213> ORGANISM: Artificial
<220> FEATURE:
<223> OTHER INFORMATION: Hu1A4A1IgG1-Furin Amino Acid Sequence

<400> SEQUENCE: 12

```
Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Lys Ala Ser

```
Asn Ser Gly Ala Leu Thr Ser Gly Val His Thr Phe Pro Ala Val Leu
                405                 410                 415
Gln Ser Ser Gly Leu Tyr Ser Leu Ser Ser Val Val Thr Val Pro Ser
            420                 425                 430
Ser Ser Leu Gly Thr Gln Thr Tyr Ile Cys Asn Val Asn His Lys Pro
        435                 440                 445
Ser Asn Thr Lys Val Asp Lys Lys Val Glu Pro Lys Ser Cys Asp Lys
    450                 455                 460
Thr His Thr Cys Pro Pro Cys Pro Ala Pro Glu Leu Leu Gly Gly Pro
465                 470                 475                 480
Ser Val Phe Leu Phe Pro Pro Lys Pro Lys Asp Thr Leu Met Ile Ser
                485                 490                 495
Arg Thr Pro Glu Val Thr Cys Val Val Val Asp Val Ser His Glu Asp
            500                 505                 510
Pro Glu Val Lys Phe Asn Trp Tyr Val Asp Gly Val Glu Val His Asn
        515                 520                 525
Ala Lys Thr Lys Pro Arg Glu Glu Gln Tyr Asn Ser Thr Tyr Arg Val
    530                 535                 540
Val Ser Val Leu Thr Val Leu His Gln Asp Trp Leu Asn Gly Lys Glu
545                 550                 555                 560
Tyr Lys Cys Lys Val Ser Asn Lys Ala Leu Pro Ala Pro Ile Glu Lys
                565                 570                 575
Thr Ile Ser Lys Ala Lys Gly Gln Pro Arg Glu Pro Gln Val Tyr Thr
            580                 585                 590
Leu Pro Pro Ser Arg Asp Glu Leu Thr Lys Asn Gln Val Ser Leu Thr
        595                 600                 605
Cys Leu Val Lys Gly Phe Tyr Pro Ser Asp Ile Ala Val Glu Trp Glu
    610                 615                 620
Ser Asn Gly Gln Pro Glu Asn Asn Tyr Lys Thr Thr Pro Pro Val Leu
625                 630                 635                 640
Asp Ser Asp Gly Ser Phe Phe Leu Tyr Ser Lys Leu Thr Val Asp Lys
                645                 650                 655
Ser Arg Trp Gln Gln Gly Asn Val Phe Ser Cys Ser Val Met His Glu
            660                 665                 670
Ala Leu His Asn His Tyr Thr Gln Lys Ser Leu Ser Leu Ser Pro Gly
        675                 680                 685
Lys

<210> SEQ ID NO 13
<211> LENGTH: 2175
<212> TYPE: DNA
<213> ORGANISM: Artificial
<220> FEATURE:
<223> OTHER INFORMATION: Hu1A4A1IgG1-2A DNA Sequence

<400> SEQUENCE: 13
atggacatga gggtcctcgc tcagctcctg gggctcctgc tgctctgttt cccaggtgcc      60
agatgtgata tccagatgac ccagtctcca tcctcactgt ctgcatctgt aggagacaga     120
gtcaccatca cttgtaaggc cagccaggac gtggacaccg ccgtgggctg gtatcagcag     180
aaaccagaga aagcccctaa gtccctgatc tattggagca gcaccggca caccgggggtc      240 ccatcaaggt tcagcggcag tggatctggg acagatttca ctctcaccat cagcagcctg     300
cagcctgaag attttgcaac ttattactgc caccagtaca gcagctaccc cttcaccttc     360
ggccctggga ccaaagtgga catcaaacgt acggtggctg caccatctgt cttcatcttc     420
```

```
ccgccatctg atgagcagtt gaaatctgga actgcctctg ttgtgtgcct gctgaataac    480
ttctatccca gagaggccaa agtacagtgg aaggtggata cgccctcca atcgggtaac    540 tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtgc accggtgaaa    720
cagactttga attttgacct tctcaagttg gcgggagacg tcgagtccaa ccctgggccc    780
atggggtcaa ccgccatcct cgccctcctc ctggctgttc tccaaggagt ctgttccgag    840
gtgcaactag tgcagtctgg agcagaggtg aaaaagcccg gggagtctct gaagatctcc    900
tgtaagggtt ctggatacag ctttaccgac taccatgtgc actgggtgcg ccagatgccc    960
gggaaaggcc tggagtggat ggggatgacc taccccggct cgacaacac caactacagc    1020 gagaccttca agggccaggt caccatctca gccgacaagt ccatcagcac cgcctacctg    1080
cagtggagca gcctgaaggc ctcggacacc gccatgtatt actgtgcgag aggcgtgggc    1140
ctggactact ggggccaagg aaccctggtc accgtctcct cagctagcac caagggccca    1200
tcggtcttcc ccctggcacc ctcctccaag agcacctctg gggcacagc ggccctgggc    1260 tgcctggtca aggactactt ccccgaaccg gtgacggtgt cgtggaactc aggcgccctg    1320
accagcggcg tgcacacctt cccggctgtc ctacagtcct caggactcta ctccctcagc    1380
agcgtggtga ccgtgccctc agcagcttg ggcacccaga cctacatctg caacgtgaat    1440
cacaagccca gcaacaccaa ggtggacaag aaagttgagc ccaaatcttg tgacaaaact    1500
cacacgtgcc caccgtgccc agcacctgaa ctcctggggg gaccgtcagt cttcctcttc    1560
cccccaaaac ccaaggacac cctcatgatc tcccggaccc ctgaggtcac atgcgtggtg    1620
gtggacgtga gccacgaaga ccctgaggtc aagttcaact ggtacgtgga cggcgtggag    1680
gtgcataatg ccaagacaaa gccgcgggag gagcagtaca acagcacgta ccgggtggtc    1740
agcgtcctca ccgtcctgca ccaggactgg ctgaatggca aggagtacaa gtgcaaggtc    1800
tccaacaaag ccctcccagc ccccatcgag aaaaccatct ccaaagccaa agggcagccc    1860
cgagaaccac aggtgtacac cctgccccca tcccgggatg agctgaccaa gaaccaggtc    1920
agcctgacct gcctggtcaa aggcttctat cccagcgaca tcgccgtgga gtgggagagc    1980
aatgggcagc cggagaacaa ctacaagacc acgcctcccg tgctggactc cgacggctcc    2040
ttcttcctct acagcaagct caccgtggac aagagcaggt ggcagcaggg gaacgtcttc    2100
tcatgctccg tgatgcatga ggctctgcac aaccactaca cgcagaagag cctctccctg    2160
tctccgggta aatga    2175
```

<210> SEQ ID NO 14
<211> LENGTH: 724
<212> TYPE: PRT
<213> ORGANISM: Artificial
<220> FEATURE:
<223> OTHER INFORMATION: Hu1A4A1IgG1-2A Amino Acid Sequence

<400> SEQUENCE: 14

```
Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
                20                  25                  30

Leu Ser Ala Ser Val Gly Asp Arg Val Thr Ile Thr Cys Lys Ala Ser
        35                  40                  45
```

-continued

```
Gln Asp Val Asp Thr Ala Val Gly Trp Tyr Gln Gln Lys Pro Glu Lys
 50                  55                  60

Ala Pro Lys Ser Leu Ile Tyr Trp Ser Ser Thr Arg His Thr Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys His Gln
                100                 105                 110

Tyr Ser Ser Tyr Pro Phe Thr Phe Gly Pro Gly Thr Lys Val Asp Ile
                115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
                195                 200                 205

Glu Lys His Lys Val Tyr Ala Cys Glu Val Thr His Gln Gly Leu Ser
                210                 215                 220

Ser Pro Val Thr Lys Ser Phe Asn Arg Gly Glu Cys Ala Pro Val Lys
225                 230                 235                 240

Gln Thr Leu Asn Phe Asp Leu Leu Lys Leu Ala Gly Asp Val Glu Ser
                245                 250                 255

Asn Pro Gly Pro Met Gly Ser Thr Ala Ile Leu Ala Leu Leu Leu Ala
                260                 265                 270

Val Leu Gln Gly Val Cys Ser Glu Val Gln Leu Val Gln Ser Gly Ala
                275                 280                 285

Glu Val Lys Lys Pro Gly Glu Ser Leu Lys Ile Ser Cys Lys Gly Ser
                290                 295                 300

Gly Tyr Ser Phe Thr Asp Tyr His Val His Trp Val Arg Gln Met Pro
305                 310                 315                 320

Gly Lys Gly Leu Glu Trp Met Gly Met Thr Tyr Pro Gly Phe Asp Asn
                325                 330                 335

Thr Asn Tyr Ser Glu Thr Phe Lys Gly Gln Val Thr Ile Ser Ala Asp
                340                 345                 350

Lys Ser Ile Ser Thr Ala Tyr Leu Gln Trp Ser Ser Leu Lys Ala Ser
                355                 360                 365

Asp Thr Ala Met Tyr Tyr Cys Ala Arg Gly Val Gly Leu Asp Tyr Trp
                370                 375                 380

Gly Gln Gly Thr Leu Val Thr Val Ser Ser Ala Ser Thr Lys Gly Pro
385                 390                 395                 400

Ser Val Phe Pro Leu Ala Pro Ser Ser Lys Ser Thr Ser Gly Gly Thr
                405                 410                 415

Ala Ala Leu Gly Cys Leu Val Lys Asp Tyr Phe Pro Glu Pro Val Thr
                420                 425                 430

Val Ser Trp Asn Ser Gly Ala Leu Thr Ser Gly Val His Thr Phe Pro
                435                 440                 445

Ala Val Leu Gln Ser Ser Gly Leu Tyr Ser Leu Ser Ser Val Val Thr
                450                 455                 460

Val Pro Ser Ser Ser Leu Gly Thr Gln Thr Tyr Ile Cys Asn Val Asn
465                 470                 475                 480
```

```
His Lys Pro Ser Asn Thr Lys Val Asp Lys Val Glu Pro Lys Ser
            485                 490                 495
Cys Asp Lys Thr His Thr Cys Pro Pro Cys Pro Ala Pro Glu Leu Leu
            500                 505                 510
Gly Gly Pro Ser Val Phe Leu Phe Pro Pro Lys Pro Lys Asp Thr Leu
            515                 520                 525
Met Ile Ser Arg Thr Pro Glu Val Thr Cys Val Val Val Asp Val Ser
    530                 535                 540
His Glu Asp Pro Glu Val Lys Phe Asn Trp Tyr Val Asp Gly Val Glu
545                 550                 555                 560
Val His Asn Ala Lys Thr Lys Pro Arg Glu Glu Gln Tyr Asn Ser Thr
                565                 570                 575
Tyr Arg Val Val Ser Val Leu Thr Val Leu His Gln Asp Trp Leu Asn
                580                 585                 590
Gly Lys Glu Tyr Lys Cys Lys Val Ser Asn Lys Ala Leu Pro Ala Pro
            595                 600                 605
Ile Glu Lys Thr Ile Ser Lys Ala Lys Gly Gln Pro Arg Glu Pro Gln
        610                 615                 620
Val Tyr Thr Leu Pro Pro Ser Arg Asp Glu Leu Thr Lys Asn Gln Val
625                 630                 635                 640
Ser Leu Thr Cys Leu Val Lys Gly Phe Tyr Pro Ser Asp Ile Ala Val
                645                 650                 655
Glu Trp Glu Ser Asn Gly Gln Pro Glu Asn Asn Tyr Lys Thr Thr Pro
            660                 665                 670
Pro Val Leu Asp Ser Asp Gly Ser Phe Phe Leu Tyr Ser Lys Leu Thr
            675                 680                 685
Val Asp Lys Ser Arg Trp Gln Gln Gly Asn Val Phe Ser Cys Ser Val
            690                 695                 700
Met His Glu Ala Leu His Asn His Tyr Thr Gln Lys Ser Leu Ser Leu
705                 710                 715                 720
Ser Pro Gly Lys
```

HUMANIZED ANTI-VENEZUELAN EQUINE ENCEPHALITIS VIRUS RECOMBINANT ANTIBODIES

CROSS REFERENCE TO PRIOR APPLICATIONS

The present application is a National Entry of PCT Application number PCT/CA2008/001940, filed on Nov. 3, 2008, which is a Continuation in Part of U.S. patent application Ser. No. 11/933,948, filed on Nov. 1, 2007 now abandoned and which claims priority from Canadian patent application number 2,607,771 filed on Nov. 1, 2007. The entire contents of the above mentioned prior applications are incorporated herein by reference.

FIELD OF THE INVENTION

The present invention relates to a humanized antibodies (Abs) and, more specifically, to humanized recombinant antibodies (rAbs) against infection by the Venezuelan equine encephalitis virus (VEEV). The invention provides methods of prophylaxis and treatment against VEEV using such antibodies.

BACKGROUND OF THE INVENTION

Venezuelan equine encephalitis virus (VEEV), a member of the alphavirus genus of the family Togaviridae, is an important mosquito-borne pathogen in humans and equides [1]. VEEV infections mainly target the central nervous system and lymphoid tissues causing severe encephalitis in equines and a spectrum of human diseases ranging from unapparent or sub-clinical infection to acute encephalitis. Neurological disease appears in 4-14% of cases. The incidence of human infection during equine epizootics could be up to 30%. Mortality associated with the encephalitis in children is as high as 35%. Recent outbreaks in Venezuela and Colombia in 1995 resulted in around 100,000 human cases with more than 300 fatal encephalitis cases [2]. Furthermore, VEEV is highly infectious by aerosol inhalation in humans and other animals. However, there are no antiviral drugs available that are effective against VEEV although currently there are two forms of IND (investigational new drug) VEEV vaccines available for human and veterinary use: TC-83, a live-attenuated Trinidad donkey strain and C-84, a formalin-inactivated TC-83 [3,4]. However, for various reasons, these vaccines are far from satisfactory. For example, approximately 20% of recipients that receive the TC-83 vaccine fail to develop neutralizing Abs, while another 20% exhibit reactogenicity. In addition, the TC-83 vaccine could revert to wild-type form. The vaccine C-84 is well tolerated, but requires multiple immunizations, periodic boosts, and fails to provide protection against aerosol challenge in some rodent models.

Like the other alphaviruses, VEEV is an enveloped virus, consisting of three structural proteins: a capsid encapsidating the viral RNA genome, and two envelope glycoproteins, E1 and E2. E1 and E2 form heterodimers, which project from the virus envelope as trimer spikes. Epitopes on the spikes are the targets of neutralizing Abs. Studies have shown that the viral neutralizing epitopes are mainly located on the E2 protein, and that the E2C epitope appears to be the hub of the neutralization epitopes [5,6]. The murine monoclonal Ab (mAb) 1A4A1 [14] is specific for E2C. This mAb has been shown to be efficient in protecting animals from a lethal peripheral challenge with virulent VEEV [7].

Murine mAbs, however, have serious disadvantages as therapeutic agents in humans [8]. For example, one of the problems associated with using murine mAbs in humans is that they may induce an anti-mouse Ab response. Further, repeat administration of murine mAbs may result in rapid clearance of the murine mAbs and anaphylaxis, which can sometimes be fatal. To overcome this hurdle, the humanization of murine mAbs has been proposed, by which process murine Ab frameworks are replaced by human Ab ones in order to reduce immunogenicity of Abs in humans [9,10].

An effective means of immunization against VEEV is needed. In particular, a means of prophylaxis against VEEV and/or a therapy for VEEV infection is desired.

SUMMARY OF THE INVENTION

In one aspect, the present invention provides prophylaxis and post-exposure therapy against VEEV infection.

In one aspect, the invention provides a humanized rAb comprising a human immunoglobulin (Ig) framework and having grafted thereon complementarity determining regions (CDRs) from the murine mAb 1A4A1. In a preferred embodiment, the human Ig framework is obtained from IgG1.

In another aspect, the invention provides a humanized rAb having specificity to the E2 envelope protein of VEEV. More specifically, the rAb has specificity to the $E2^c$ epitope of the E2 protein.

In another aspect, the invention provides a humanized rAb wherein the complementarity determining regions CDR1, CDR2 and CDR3 of the heavy chain variable region (VH) have the following amino acid sequences:
    CDR1: SEQ ID NO: 1
    CDR2: SEQ ID NO: 2
    CDR3: SEQ ID NO: 3
In another aspect, the invention provides a humanized rAb wherein the complementarity determining regions CDR1, CDR2 and CDR3 of the light chain variable region (VL) have the following amino acid sequences:
    CDR1: SEQ ID NO: 4
    CDR2: SEQ ID NO: 5
    CDR3: SEQ ID NO: 6.
In a further aspect, the invention provides a humanized rAb having a VH comprising the amino acid sequence of SEQ ID NO: 7.

In a further aspect, the invention provides a humanized rAb having a VL comprising the amino acid sequence of SEQ ID NO: 8.

In another aspect, the invention provides a DNA sequence which encodes a polypeptide corresponding to a CDR grafted VH having the amino acid sequence according to SEQ ID NO: 7.

In another aspect, the invention provides a DNA sequence which encodes a polypeptide corresponding to a CDR grafted VL having the amino acid sequence according to SEQ ID NO: 8.

In a further aspect, the invention provides a DNA construct having a nucleic acid sequence according to SEQ ID NO:11 or SEQ ID NO:13.

In another aspect, the invention provides an expressed protein comprising a humanized rAb having an amino acid sequence according to SEQ ID NO: 12 or SEQ ID NO: 14.

The invention provides vectors containing such DNA sequences and host cells transformed thereby.

In other aspects, the invention provides methods and uses for treatment and/or prophylaxis against VEEV infection comprising the antibodies described herein. The invention also provides pharmaceutical preparations for such treatment or prophylaxis.

BRIEF DESCRIPTION OF THE DRAWINGS

These and other features of the invention will become more apparent in the following detailed description in which reference is made to the appended drawings wherein:

FIGS. 3a to 3c schematically illustrate the humanization of the murine Ab variable region.

FIG. 5 schematically illustrates the humanization of the Ab VH and shows its amino acid sequence (SEQ ID NO: 7).

FIG. 6 schematically illustrates the humanization of the Ab VL and shows its amino acid sequence (SEQ ID NO: 8).

DETAILED DESCRIPTION OF THE INVENTION

Figure 1:
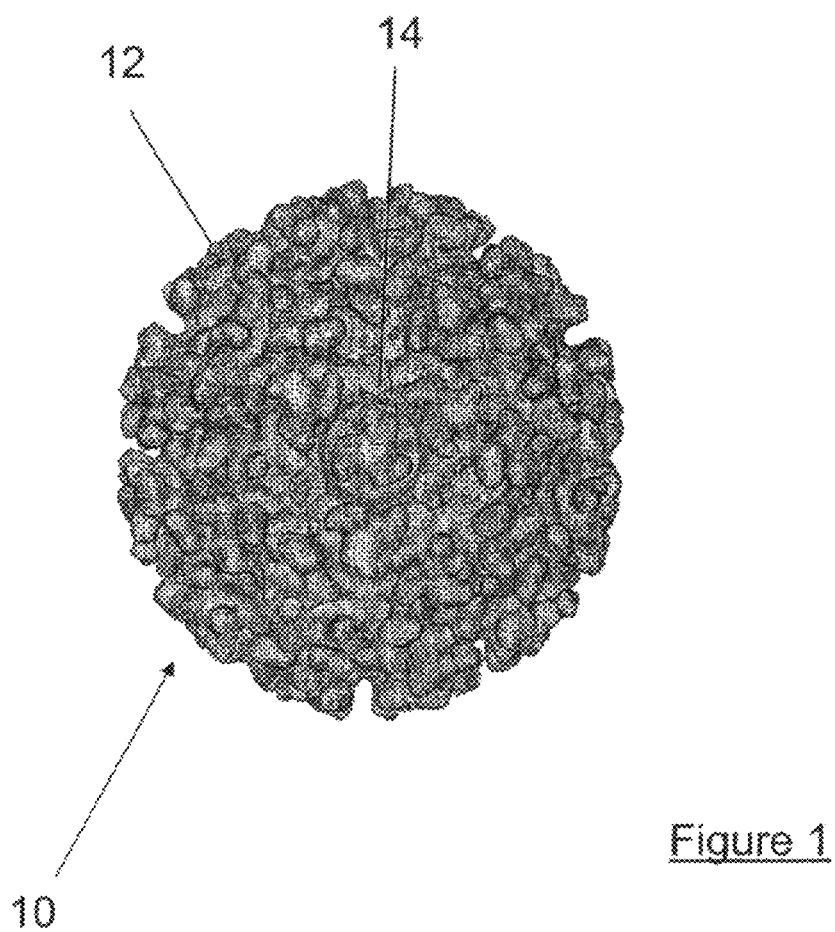
FIG. 1 is a representation of the external structure of the VEEV.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "recombinant antibody", as used herein, refers to antibodies that are prepared, expressed, created or isolated by recombinant means, such as (a) antibodies isolated from an animal (e.g., a mouse) that is transgenic or transchromosomal for immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

As used herein the terms "expression vector" or "cloning vector" include vectors which are designed to provide transcription of the nucleic acid sequence. The transcribed nucleic acid may be translated into a polypeptide or protein product. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors" or "cloning vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operatively-linked" or "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are well known in the art such as, for example, in Goeddel, Gene Expression Technology: Methods in Enzymology 185, Academic Press, San Diego, Calif. (1990). Regulatory sequences include those that direct constitutive expression of a nucleotide sequence in many types of host cells and those that direct expression of the nucleotide sequence only in certain host cells (e.g., tissue-specific regulatory sequences) or inducible promoters (e.g., induced in response to abiotic factors such as environmental conditions, heat, drought, nutrient status or physiological status of the cell or biotic such as pathogen responsive). Examples of suitable promoters include for example constitutive promoters, ABA inducible promoters, tissue specific promoters and abiotic or biotic inducible promoters. It will be appreciated by those skilled in the art that the design of the expression vector can depend on such factors as the choice of the host cell to be transformed, the level of expression of protein desired as well as timing and location of expression, etc. The expression vectors of the invention can be introduced into host cells to thereby produce proteins or peptides, including fusion proteins or peptides, encoded by nucleic acids as described herein.

The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

FIG. 1 illustrates the external structure of the VEEV. As shown, the virus 10 includes a nucleocapsid 12 enveloping the viral RNA genome. The envelope comprises glycoproteins E1 and E2, arranged in the form of heterodimers 14. Protein E2, which is responsible for viral attachment to the host cell, contains neutralizing epitopes.

As has been described in the prior art, the murine mAb 1A4A1 has been found to be specific to the VEEV E2 envelope protein and, further, has been found to have a strong neutralizing function against VEEV. The murine mAb, however, causes a sometimes fatal allergenic reaction in humans, resulting in the formation of human anti-mouse Abs (HAMA). It is for this reason that the present inventors have sought to humanize the 1A4A1 mAb so as to provide an effective agent to counter VEEV infection in humans. In the course of this research, humanized recombinant anti-VEEV monoclonal antibodies have recently been designed and developed [18]. Such recombinant antibodies are described further herein and are the subject of Canadian patent application number 2,607,771 and U.S. patent application Ser. No. 11/933,948, both filed on Nov. 1, 2007. The present invention provides methods and uses involving such antibodies for the prevention (prophylaxis) and treatment against VEEV infection in mammals.

In vivo efficacy studies in mice have demonstrated that treatment with murine mAb 1A4A1 leads to protection of animals from a lethal peripheral challenge with virulent VEEV. Thus, the present invention builds upon these findings by providing a humanized mAb 1A4A1 to reduce the foreignness of murine mAb in humans. For doing this, the majority of the non-human protein sequence (in one embodiment, more than 90%) of mAb 1A4A1 is replaced with a human Ab sequence and the resultant whole humanized mAb gene is then synthesized and cloned to an expression vector such as an adenoviral vector. The recombinant adenoviral vector can be delivered as a therapeutic agent for prophylaxis or treatment of VEEV infection in humans. One advantage of this method is that the vector can express the humanized Ab in the human body for a long period of time. The humanized Ab can also be produced in cell culture and delivered directly as a therapeutic.

The humanization of the present anti-VEEV mAb 1A4A1 has not been done previously and particularly not for the prophylaxis or treatment of VEEV infection. The present invention provides in one embodiment a humanized Ab, referred to herein as Hu1A4A1IgG1, that retains the VEEV-binding specificity and neutralizing activity of murine 1A4A1 while not eliciting a HAMA response. As described further below, the humanized Ab comprises an Ig framework of human IgG1 and CDRs obtained from murine mAb 1A4A1. The rAb of the present invention is specific to an epitope of the E2 envelope glycoprotein of VEEV and, more specifically, to the $E2^c$ epitope thereon.

Figures 2A, 2B, 2C, 2D:
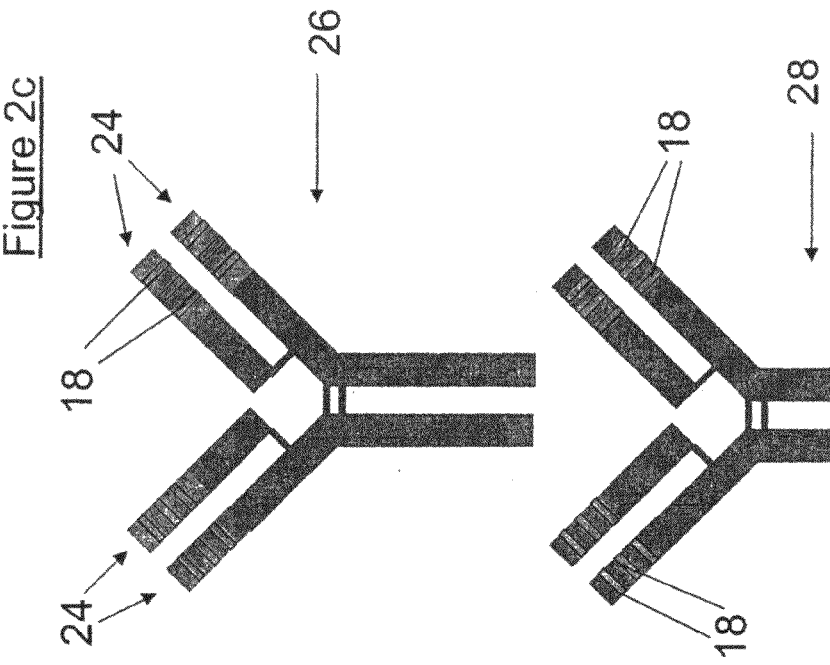
FIGS. 2a to 2d schematically illustrate murine, human, chimeric and humanized Abs, respectively.
Figure 4:
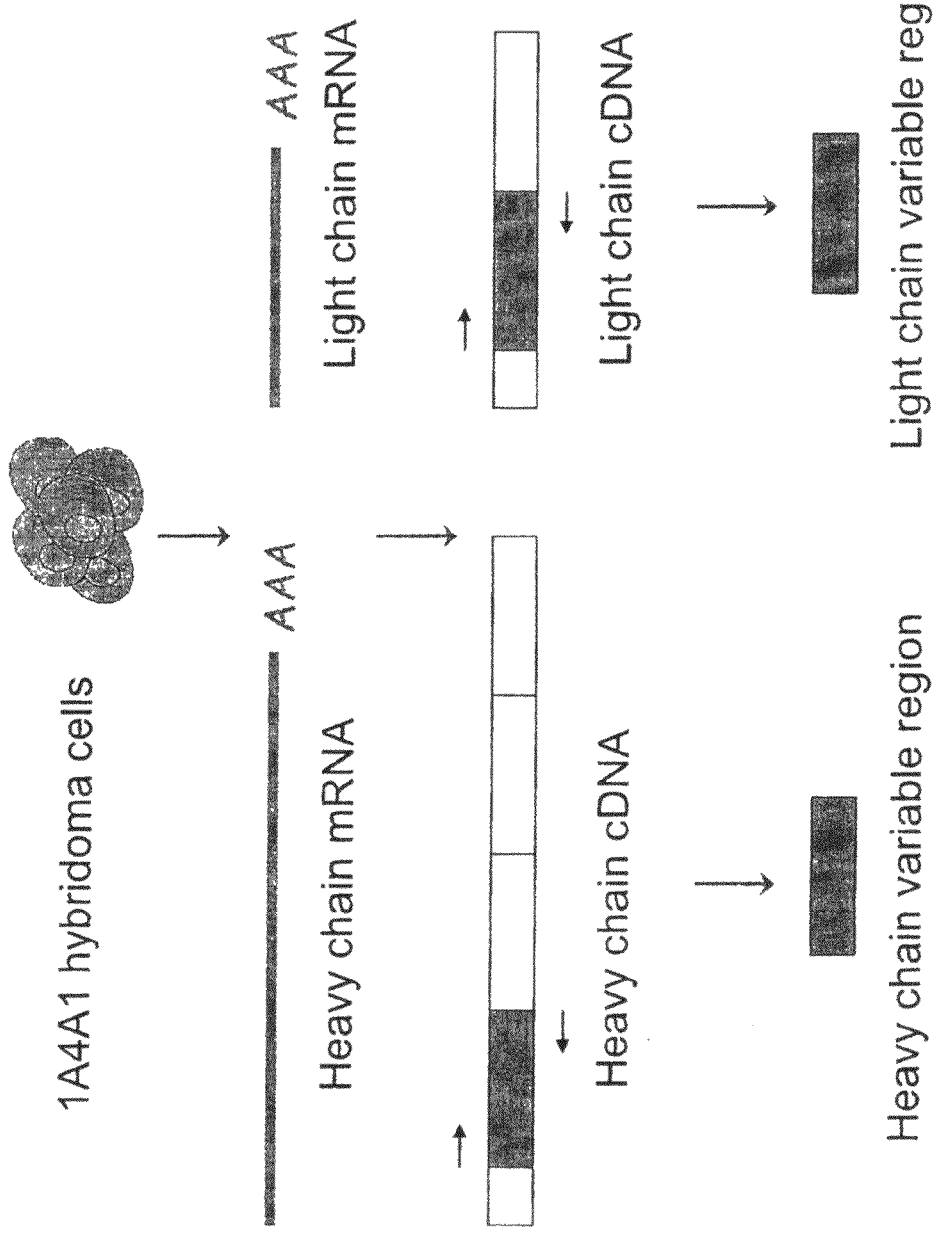
FIG. 4 schematically illustrates the cloning of the murine Ab VH and VL.

The construction of the humanized Ab of the invention is schematically illustrated in FIGS. 2a to 2d. FIG. 2a illustrates schematically the structure of a murine Ab 16 containing murine CDRs 18 on the respective variable regions. FIG. 2b shows a human Ab 20 containing human CDRs 22. As shown in FIG. 2c, a chimeric Ab 26 would comprise the murine variable regions 24, containing the murine CDRs 18, joined to the constant regions of the human Ab. On the other hand, FIG. 2d illustrates a humanized Ab 28 according to an embodiment of the invention, wherein only the murine CDRs 18 are grafted to the variable regions of the human Ab 20.

The substitution of the murine CDRs into the human Ig framework is illustrated also in FIGS. 3a to 3c. As shown, the humanized Ab variable region comprises the grafted CDRs, 18, from the murine Ab.

The protein sequences of the rAbs of the invention include linker sequences. The expressed rAbs of the invention have amino acid sequences as shown in SEQ ID NO:12 and SEQ ID NO:14. The nucleic acid constructs used in transforming cells to express the above rAbs are shown in SEQ ID NO:11 and SEQ ID NO:13.

As illustrated further below, the humanized recombinant antibodies of the present invention have been found to be effective as both a prophylaxis and a treatment against VEEV infection.

EXAMPLES

The following examples are provided to illustrate embodiments of the present invention. The examples are not intended to limit the scope of the invention in any way.

Example 1

Construction of Hu1A4A1IgG1 and In Vitro Studies

In the study described below, murine mAb 1A4A1 CDRs of VH, VL were grafted onto the frameworks of germline variable and joining (V, J) gene segments of human Ig heavy and light chains, respectively, which were chosen based on the CDR similarities between human Igs and murine mAb 1A4A1. Furthermore, the humanized VH and VL were, respectively, grafted onto human gamma 1 heavy chain constant regions (CHs) and kappa 1 light chain constant region (CL) to assemble the whole humanized Ab gene. The resultant whole humanized mAb gene was synthesized and cloned to an adenoviral vector. After the humanized Ab was expressed in HEK 293 cells and purified with protein L column, the Ab was demonstrated to retain antigen-binding specificity and neutralizing activity.

Materials and Methods

Humanization of Murine mAb 1A4A1

Murine mAb 1A4A1 was provided by Dr. J. T. Roehrig (Division of Vector-borne Infectious Diseases, Centers for Disease Control and Prevention, Fort Colins, Colo., USA). The VH and VL of mAb 1A4A1 were cloned in a single chain variable fragment (ScFv) format, mA116 previously [7], which showed to retain the same binding specificity as mAb 1A4A1 [11]. The humanization of VH and VL of murine mAb 1A4A1 was done by Absalus Inc. (Mountain View, Calif., USA). Briefly, in order to select human VH and VL frameworks 1-3, the VH and VL amino acid sequences of murine 1A4A1 were separately subjected to IgBlast and IMGT searches against the entire human Ig germline V gene segments and then human heavy and light chain germline V gene segments were selected based on their highest CDR 1 and 2 similarities with those of murine 1A4A1 VH and VL without consideration of framework similarity. Both human VH and VL framework 4 were selected, respectively, from human heavy and light chain J gene segments based on the highest similarities between human J gene segments and murine 1A4A1 VH and VL CDR3. Finally, CDRs of murine 1A4A1 VH and VL were, respectively, grafted onto the frameworks of selected germline V and J gene segments of human Ab heavy and light chains, resulting in humanized 1A4A1 (Hu1A4A1). Furthermore, the Hu1A4A1 VH and VL were, respectively, grafted onto human gamma 1 heavy chain CHs and kappa 1 light chain CL to assemble the whole humanized Ab gene, resulting in humanized 1A4A1IgG1 (Hu1A4A1IgG1). This process is illustrated in FIGS. 3 to 6.

Construction, Expression and Purification of Hu1A4A1IgG1 (Hu1A4A1IgG1-furin and Hu1A4A1IgG1-2A)

Figure 7:
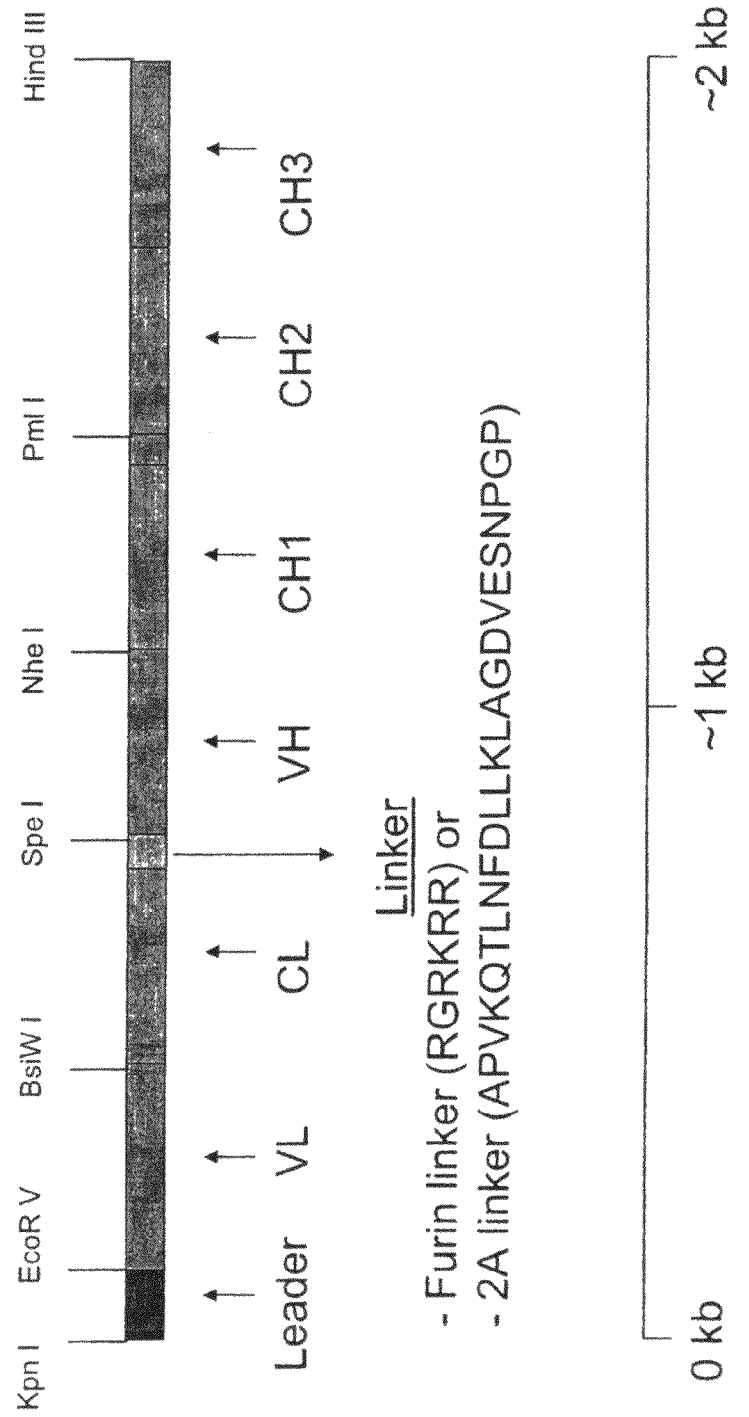
FIG. 7 schematically illustrates the design of a full Hu1A4A1IgG1 rAb gene in a single open reading frame with two versions, Hu1A4A1IgG1-furin (SEQ ID NO: 11) and Hu1A4A1IgG1-2A (SEQ ID NO: 13).

The Hu1A4A1IgG1 DNA sequence (~2 kb) is schematically illustrated in FIG. 7. The nucleic acid sequence of the Hu1A4A1IgG1-furin rAb is provided in SEQ ID NO:11 and the nucleic acid sequence of the Hu1A4A1IgG1-2A rAb is provided in SEQ ID NO:13.

The Hu1A4A1IgG1 DNA sequences were synthesized as follows. As shown in FIG. 7, a light chain leader sequence was provided upstream from the light chain, followed by a furin or 2A linker (discussed further below) before the heavy chain. The whole DNA sequence flanked by Kpn I and Hind III was synthesized by GenScript Corporation (Scotch Plaines, N.J., USA) and cloned into pUC57 vector, resulting in pUC57-Hu1A4A1IgG1-furin or pUC57-Hu1A4A1IgG1-2A.

Figure 8:
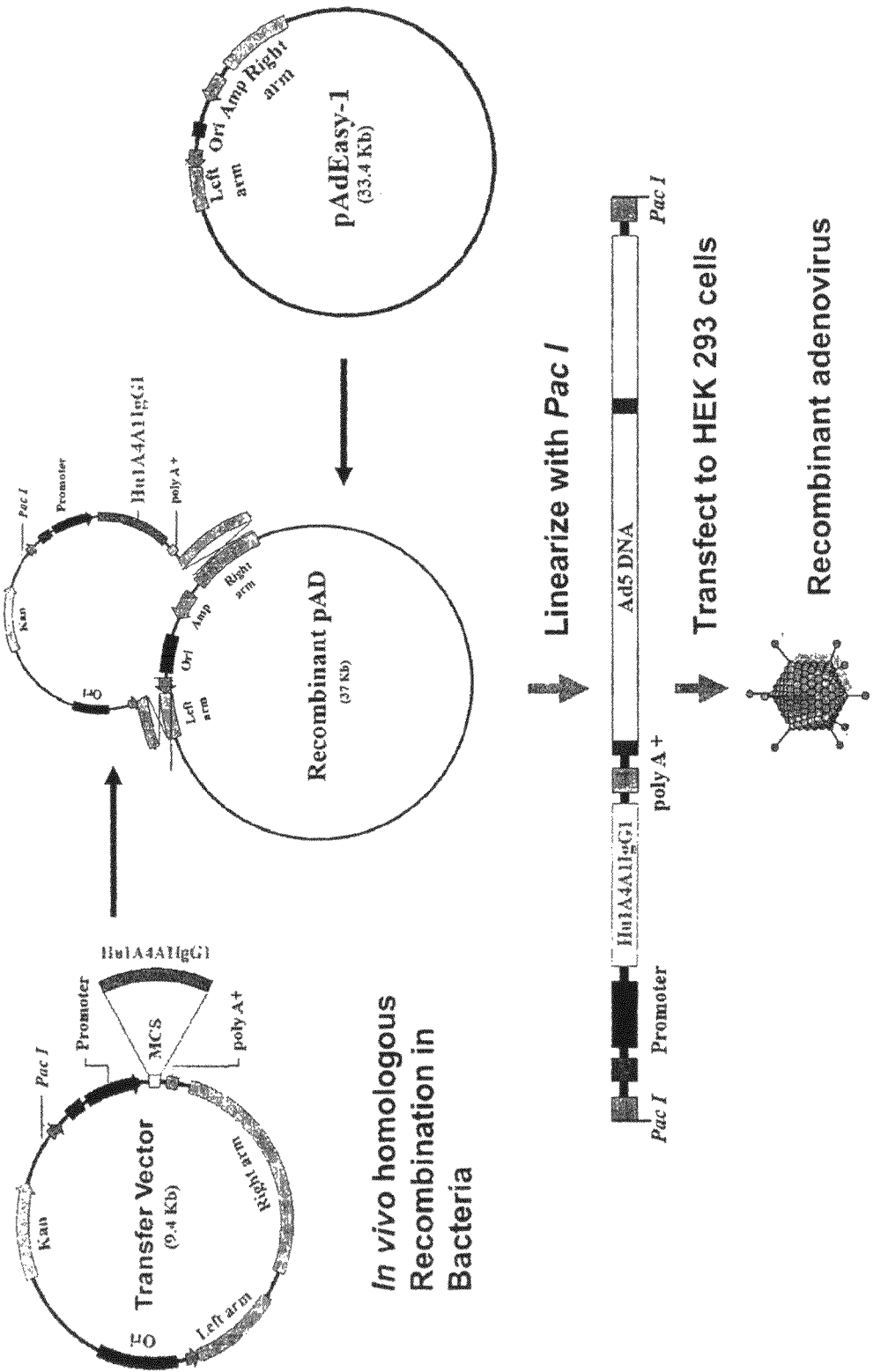
FIG. 8 schematically illustrates the cloning of the Hu1A4A1IgG1-furin and Hu1A4A1IgG1-2A genes into an adenoviral vector respectively.

Recombinant adenovirus vectors expressing either Hu1A4A1IgG1-furin or Hu1A4A1IgG1-2A were constructed using AdEasy™ system (Qbiogene, Carlsbad, Calif., USA) according to the manufacturer's protocol. Briefly, the Kpn I-Hind III fragment of Hu1A4A1IgG1-furin or Hu1A4A1IgG1-2A was ligated to a Kpn I-Hind III-digested pShuttle-CMV vector. The resulting pShuttle construct was co-transformed with the pAd Easy-1 vector into *Escherichia coli* BJ5183 cells to produce recombinant adenoviral genomic constructs for Hu1A4A1IgG1-furin or Hu1A4A1IgG1-2A proteins. The recombinant adenoviral constructs, pAd-Hu1A4A1IgG1-furin and pAd-Hu1A4A1IgG1-2A were linearized with Pac I and transfected into HEK 293 cells (American Type Culture Collection, Manassas, Va., USA) cultured in Dulbecco's Modified Eagle's Medium supplemented with 5% fetal bovine serum (FBS) for amplification and then the amplified adenovirus was purified by a chromatographic method. This procedure is illustrated in FIG. 8.

Figure 9:
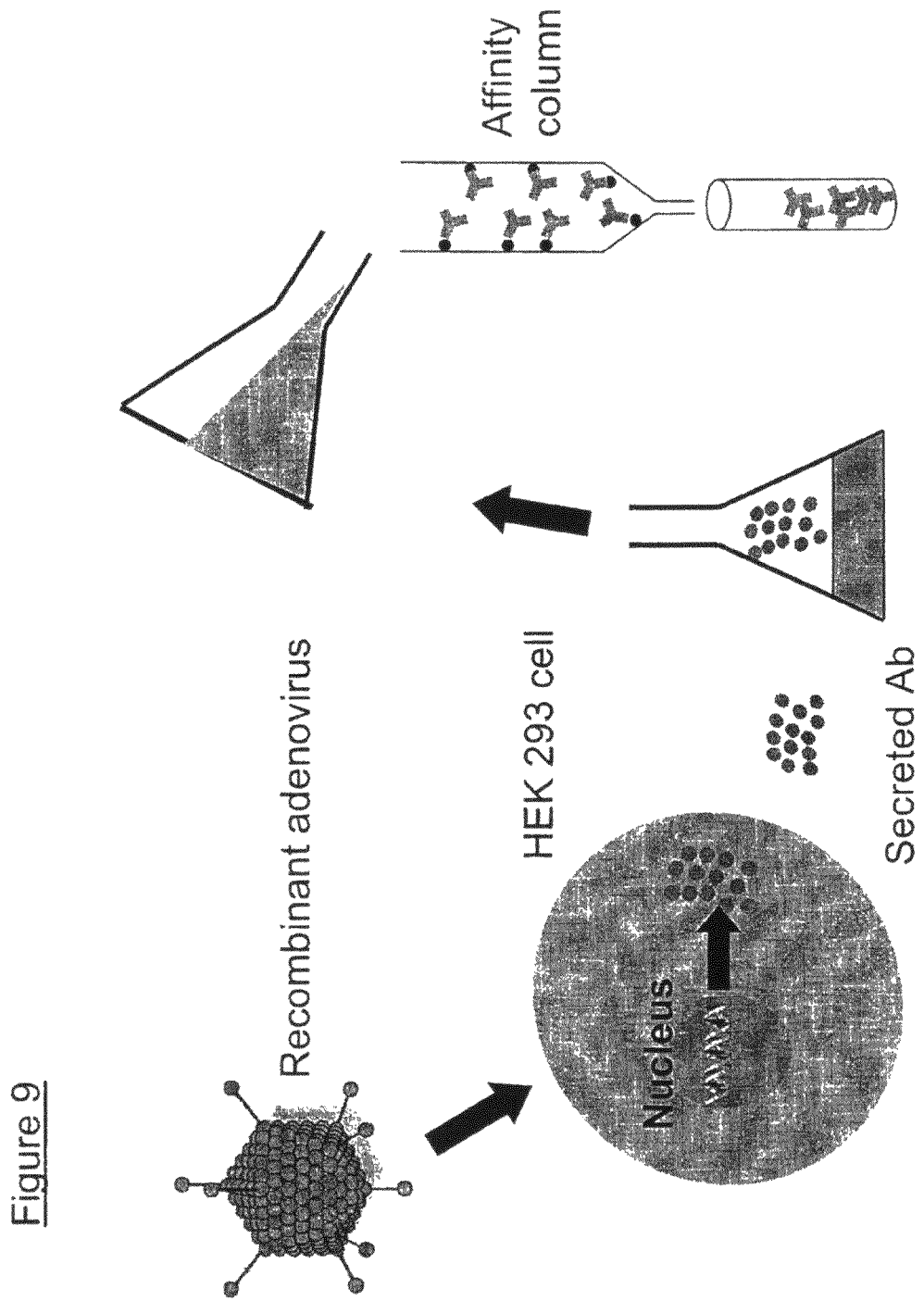
FIG. 9 schematically illustrates expression and purification of the Hu1A4A1IgG1-furin and Hu1A4A1IgG1-2A rAbs.

As illustrated in FIG. 9, the expression of Hu1A4A1IgG1-furin or Hu1A4A1IgG1-2A was achieved by first infecting HEK 293 cells with the recombinant adenovirus pAd-Hu1A4A1IgG1-furin or pAd-Hu1A4A1IgG1-2A at a multiplicity of infection (MOI) of 1. The infected cells were cultured for one week and the culture supernatant was harvested. The expressed Hu1A4A1IgG1-furin or Hu1A4A1IgG1-2A was purified using protein L agarose gel from Pierce (Brockville, Ont., Canada). Briefly, culture supernatant was dialyzed against phosphate buffer saline (PBS) (Sigma-Aldrich, Oakville, Ont., Canada) for 12 h and then concentrated using PEG (Sigma-Aldrich) to less than 50 ml. The concentrated sample was incubated with 2 ml protein L agarose gel at 4° C. for 1 h. The gel and supernatant mixture was then loaded to an empty column, which was subsequently washed with binding buffer. Bound Hu1A4A1IgG1-furin or Hu1A4A1IgG1-2A was eluted with elution buffer. The eluted Ab was further desalted using an excellulose column (Pierce) and then concentrated by a Centracon™ YM-30 (Millipore Corp., Bedford, Mass., USA).

The amino acid sequence of the expressed Hu1A4A1IgG1-furin is shown in SEQ ID NO:12 and the amino acid sequence of the expressed Hu1A4A1IgG1-2A is shown in SEQ ID NO:14.

Cells that were transformed to express the Hu1A4A1IgG1-furin and Hu1A4A1IgG1-2A humanized antibodies have been deposited at the International Depositary Authority of Canada (IDAC) (National Microbiology Laboratory, Winnipeg, Manitoba, Canada) under accession numbers 141107-01 and 141107-02, respectively.

SDS-PAGE

Figure 10:
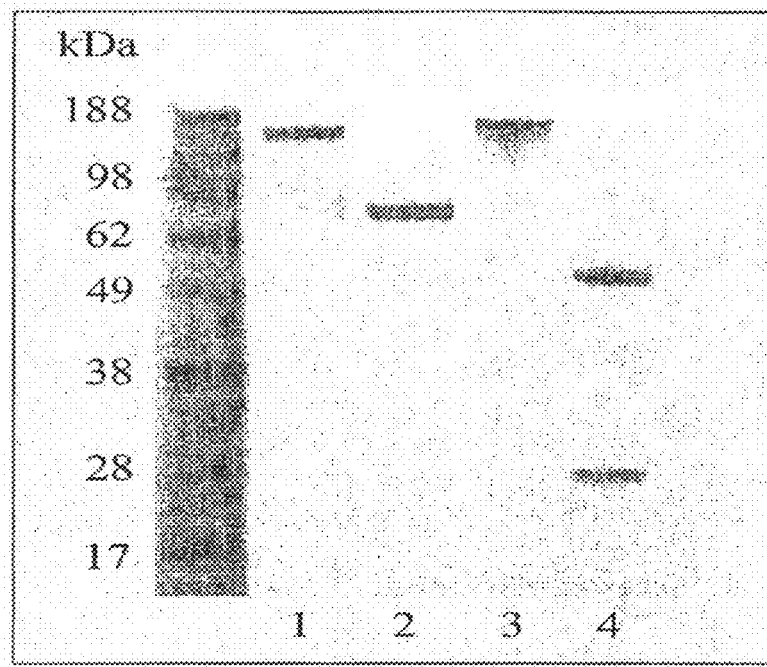
FIGS. 10 and 11 illustrate the results from the SDS-PAGE separation of the produced Hu1A4A1IgG1-furin rAb.
Figure 11:
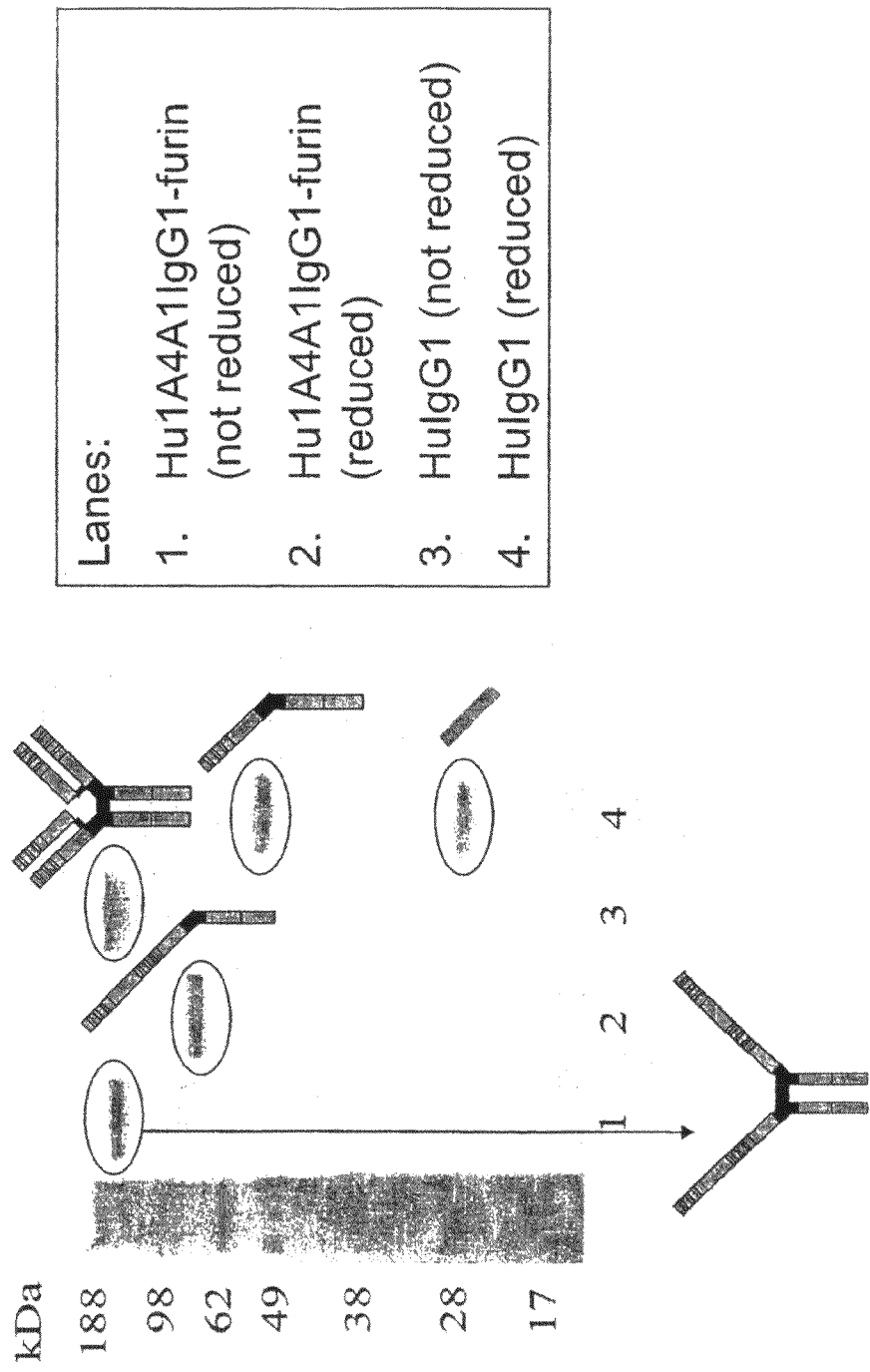
Figure 12:
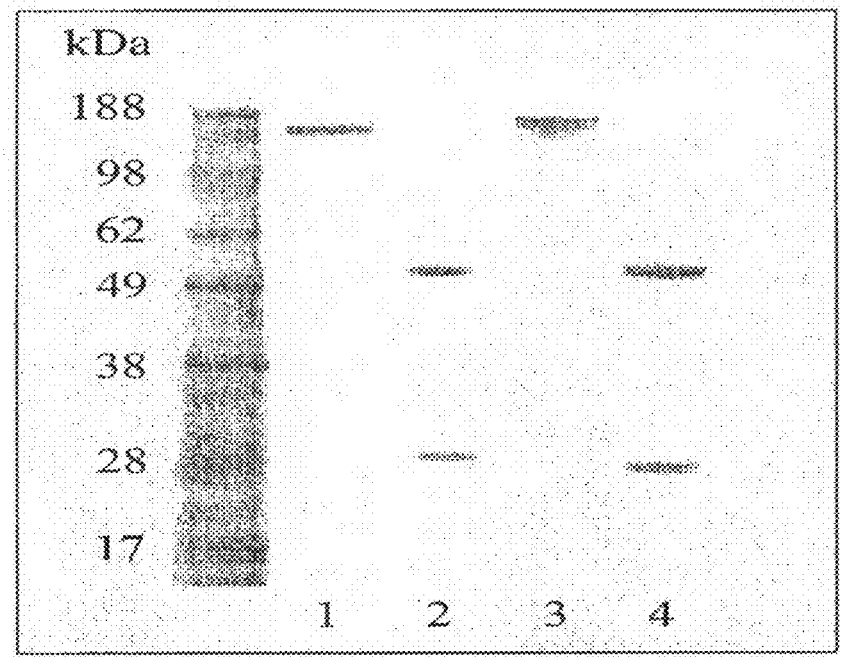
FIG. 12 illustrates the results from the sodium dodecyl sulfate-polyacrylamide gel electrophoresis (SDS-PAGE) separation of the produced Hu1A4A1IgG1-2A rAb.

Abs were separated by 10% SDS-PAGE gels using a Mini-PROTEAN™ II apparatus (Bio-Rad Laboratories, Mississauga, Ont., Canada). The bands were visualized by Simply-Blue™ safestain staining (Invitrogen, Burlington, Ont., Canada). The molecular weights of the samples were estimated by comparison to the relative mobility values of standards of known molecular weights. The SDS-PAGE analyses of the purified Hu1A4A1IgG1-furin are illustrated in FIGS. 10 and 11. FIG. 12 illustrates the SDS-PAGE analysis of the purified Hu1A4A1IgG1-2A. As shown, lanes 1 and 3 correspond to purified Hu1A4A1IgG1 and control human IgG1 in a non-reducing condition and lanes 2 and 4 correspond to purified Hu1A4A1IgG1 and control human IgG1 in a reducing condition.

ELISA

Figure 13:
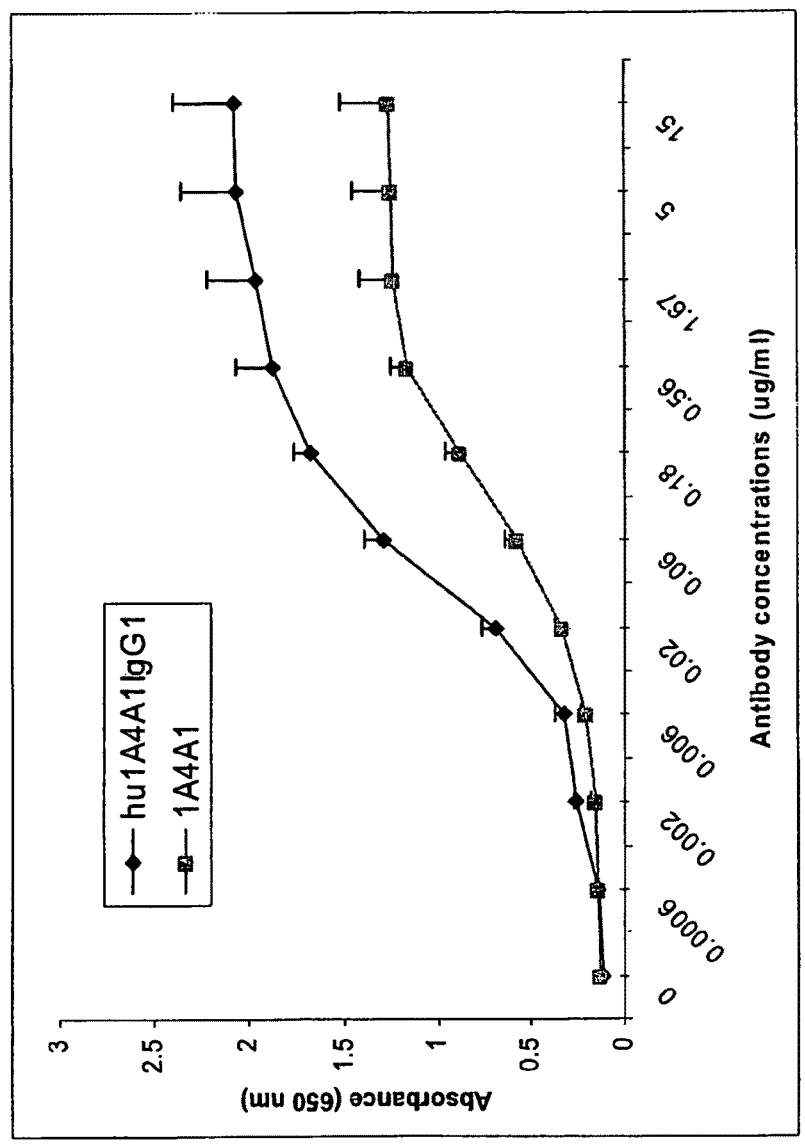
FIG. 13 illustrates the results of the enzyme-linked immunosorbent assays (ELISA) for the reactivity of the Hu1A4A1IgG1-furin and Hu1A4A1IgG1-2A rAbs.

The reactivity of purified Hu1A4A1IgG1-furin or Hu1A4A1IgG1-2A to VEEV E2 antigen was determined by ELISA. Nunc Maxisorp™ flat bottomed 96-well plates (Canadian Life Technologies, Burlington, Ont., Canada) were coated overnight at 4° C. with recombinant VEEV E2 antigen at a concentration of 10 µg/ml in carbonate bicarbonate buffer, pH 9.6. The plates were washed five times with PBS containing 0.1% Tween™-20 (PBST) and then blocked in 2% bovine serum albumin for 2 h at room temperature. After five washes with PBST, the plates were incubated for 2 h at room temperature with various concentrations of Hu1A4A1IgG1-furin, Hu1A4A1IgG1-2A or 1A4A1 Abs diluted in PBST. Following five washes with PBST, the plates were incubated for 2 h at room temperature with horseradish peroxidase (HRP)-conjugated rabbit anti-human IgG fragment crystallizable portion or HRP-conjugated rabbit anti-mouse IgG (Jackson ImmunoResearch Laboratories Inc., West Grove, Pa., USA) diluted 1:5000 in PBST. Finally, the plates were washed five times with PBST and developed for 10 min at room temperature with a 3,3',5,5'-tetramethylbenzidine substrate (Kirkegaard and Perry Laboratories). The reactions were read at an absorbance of 650 nm by a microplate autoreader (Molecular Devices, Sunnyvale, Calif., USA). The results of the ELISA Hu1A4A1IgG1-antigen binding assay are illustrated in FIG. 13.

Neutralization Assay In Vitro

Figure 15:
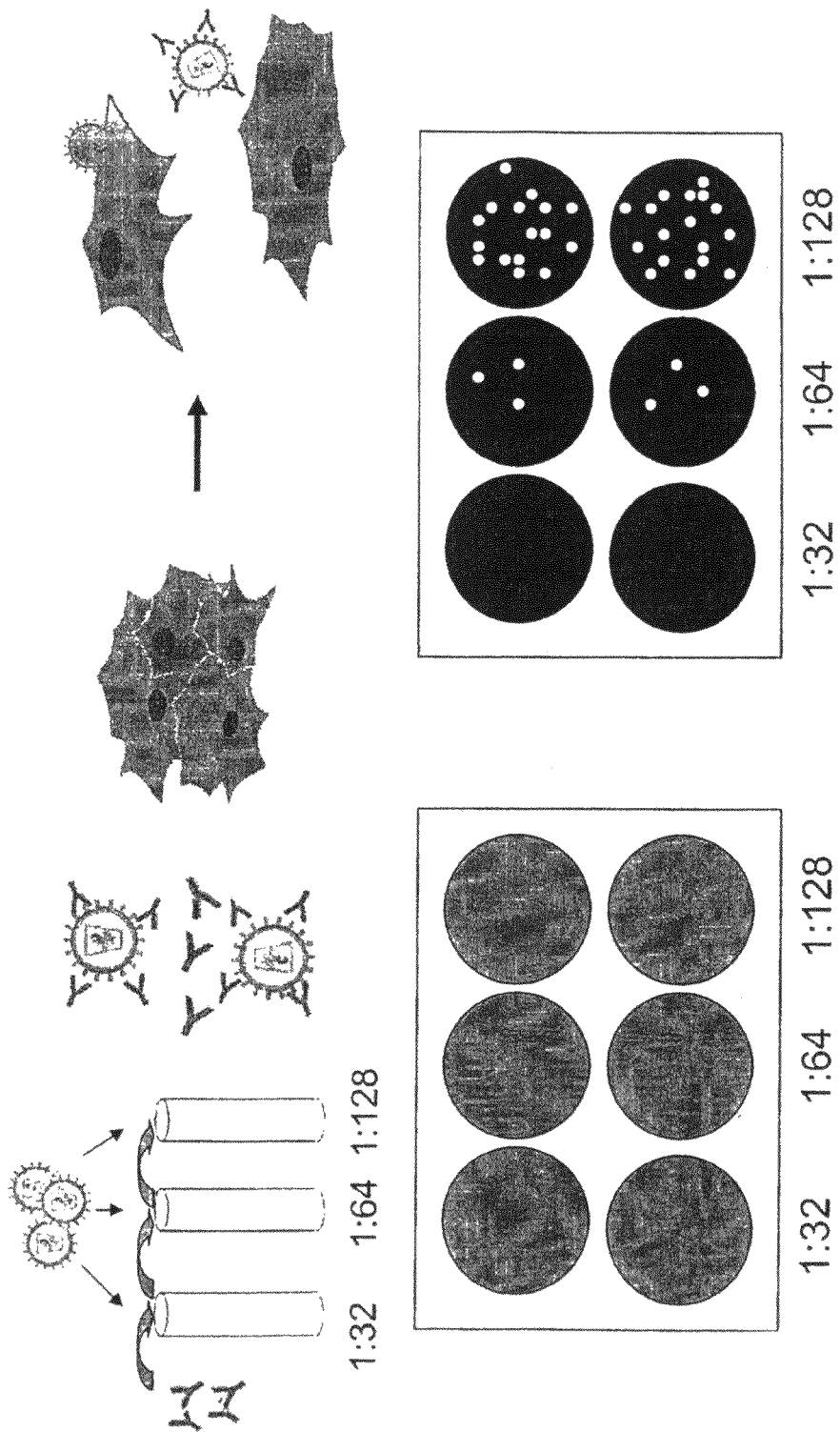
FIG. 15 schematically illustrates the neutralization assay used in assessing the neutralizing activity of the Hu1A4A1IgG1-furin and Hu1A4A1IgG1-2A rAbs against VEEV.

Neutralizing activity of each of Hu1A4A1IgG1-furin and Hu1A4A1IgG1-2A against VEEV (strain TC-83) was analyzed by a plaque reduction assay. Briefly, each Ab was serially two-fold diluted (1:32, 1:64, 1:128, etc.) and mixed with an equal volume containing 50 plaque-forming units of virus per 100 µl. Afterwards, the mixtures were incubated for 1 h at room temperature, 200 µl of the mixture was inoculated in duplicate into wells of six-well plates containing confluent Vero cell monolayers and incubated at 37° C. for 1 h. At the end of the incubation, the virus/Ab mixtures were removed from the wells before the wells were overlaid by tragacanth gum and then incubated for 2 days. The wells were stained with 0.3% crystal violet and plaques were counted. Neutralization titre was expressed as the highest Ab dilution that inhibited 50% of virus plaques. This procedure is illustrated in FIG. 15.

Results and Discussion

Different approaches have been developed to humanize murine Abs in order to reduce the antigenicity of murine Abs in humans [9,10]. One widely used approach is CDR-grafting, which involves the grafting of all murine CDRs onto a human Ab frameworks. The human Ab frameworks are chosen based on their similarities to the frameworks of the murine Ab to be humanized. The CDR-grafting approach has been proven successful in some cases. However, in many more instances, this humanization process could result in CDR conformation changes, which affect the antigen-binding affinity. To restore the affinity, additional work for back-mutation of several murine framework amino acids, which are deemed to be critical for CDR loop conformation, have to be done.

Recently, Hwang et al. [12] employed an approach which consisted of grafting CDRs onto human germline Ab frameworks based on the CDR sequence similarities between the murine and human Abs while basically ignoring the frameworks. Because the selection of the human frameworks is driven by the sequence of the CDRs, this strategy minimizes the differences between the murine and human CDRs. This approach has the potential to generate humanized Abs that retain their binding affinity to their cognate antigen. Further, since all residues in frameworks are from human Ab germline sequences, the potential immunogenicity of non-human Abs is highly reduced.

Using the above approach, and as disclosed herein, the present inventors humanized an anti-VEEV murine mAb 1A4A1. The amino acid sequences of VH and VL from murine 1A4A1 were first aligned with human Ig germline V and J genes. As shown in FIG. 5, the human heavy chain V gene segment H5-51 and J gene segment JH4 were selected to provide the frameworks for the murine 1A4A1 VH. Similarly, as shown in FIG. 6, for the murine 1A4A1 VL, the human light chain V gene segment L15 and J gene segment Jk3 were selected.

The identities of the CDR1 and CDR2 amino acid sequences between murine 1A4A1 VH and the human H5-51 gene segment were 20% and 47%, respectively, while the identity of the CDR3 between murine 1A4A1 VH and the JH4 gene segment was 33%. For the light chain, the identities of the CDR1 and CDR2 between murine 1A4A1 VL and the human L15 gene segment were 27% and 14%, respectively, while the identity of the CDR3 between murine 1A4A1 VL and human Jk3 gene segment was 22%. The CDRs of murine 1A4A1 VH were then grafted onto the frameworks of selected human Ig germline H5-51 and JH4 gene segments, while the CDRs of murine 1A4A1 VL were grafted onto human L15 and Jk3 gene segments. The hu1A4A1 VH was further grafted onto the human gamma 1 heavy chain CHs to form a complete heavy chain, while the VL was grafted onto the human kappa 1 light chain CL to form a whole humanized light chain. This procedure is schematically illustrated in FIGS. 5 and 6 with the end structure being illustrated in FIG. 7.

As shown in FIG. 5, the murine 1A4A1 VH CDRs grafted onto the human framework comprised the following amino acid sequences:

```
VH CDR1: DYHVH                 (SEQ ID NO: 1)
VH CDR2: MTYPGFDNTNYSETFKG     (SEQ ID NO: 2)
VH CDR3: GVGLDY                (SEQ ID NO: 3)
```

As shown in FIG. 6, the murine 1A4A1 VL CDRs grafted onto the human framework comprised the following amino acid sequences:

```
VL CDR1: KASQDVDTAVG      (SEQ ID NO: 4)
VL CDR2: WSSTRHT          (SEQ ID NO: 5)
VL CDR3: HQYSSYPFT        (SEQ ID NO: 6)
```

As shown in FIG. 5, the VH of the humanized Ab according to the present invention comprises the following amino acid sequence:

```
Hu-VH:
                                           (SEQ ID NO: 7)
EVQLVQSGAEVKKPGESLKISCKGSGYSFTDYHVHWVRQMPGKGLEWMGM
TYPGFDNTNYSETFKGQVTISADKSISTAYLQWSSLKASDTAMYYCARGV
GLDYWGQGTLVTVSS.
```

Thus, as shown in FIG. 6, the VL of the humanized Ab according to the present invention comprises the following amino acid sequence:

```
Hu-VL:
                                           (SEQ ID NO: 8)
DIQMTQSPSSLSASVGDRVTITCKASQDVDTAVGWYQQKPEKAPKSLIYW
SSTRHTGVPSRFSGSGSGTDFTLTISSLQPEDFATYYCHQYSSYPFTFGP
GTKVDIKR.
```

In order to express heavy and light chains in a monocistronic construct, a six-residue peptide, RGRKRR (SEQ ID NO: 9) containing the recognition site for the protease furin, designated as "furin linker", or a twenty-four-residue peptide of the foot-and-mouth-disease virus (FMDV)-derived 2A self-processing sequence, APVKQTLNFDLLKLAGD-VESNPGP (SEQ ID NO: 10), designated as "2A linker", was incorporated between the two chains. The location of the furin or 2A linker within the nucleic acid constructs of the Abs is illustrated in FIG. 7. Furin is a ubiquitous subtilisin-like proprotein convertase, which is the major processing enzyme of the secretory pathway [13]. The furin minimal cleavage site is R-X-X-R; however, the enzyme prefers the site R-X-(K/R)-R. An additional R at the P6 position appears to enhance cleavage. The FMDV-derived 2A linker is able to cleave at its own C terminus between the last two residues through an enzyme-independent but undefined mechanism, probably by ribosomal skip, during protein translation. To get the expressed Ab to be secreted to culture media, a leader sequence was added upstream to the Ab gene. FIG. 7 illustrates the synthesized DNA sequence, of approximately 2 kb, including the human Ab kappa light chain L15 leader sequence, the humanized light chain (VL+CL), the furin or 2A linker, and the humanized heavy chain (VH+CH1+CH2+CH3). This sequence was then cloned into an adenoviral vector. The unique restriction sites, as also shown in FIG. 7, flanking the V regions, which allow for efficient V region replacement and at the heavy chain V-C region junction for generation of fragment antigen-binding portion of Ab (Fab), were also designed.

Protein G and A columns are widely used for a quick purification for Abs because of protein G and A binding to the Fc portion of Ig. However, protein G and A cannot only bind to human Ig, but also bind to bovine Ig, therefore they cannot be used for purification of Hu1A4A1IgG1-furin or Hu1A4A1IgG1-2A in our study since pAd-Hu1A4A1IgG1- furin or pAd-Hu1A4A1IgG1-2A-infected HEK 293 cells were cultured in the medium with 5% FBS containing a high percentage of bovine Ig. Unlike protein G and A, protein L binds Ig through interactions with the light chains. Protein L only binds to Ig containing light chains of type kappa 1, 3 and 4 in human and kappa 1 in mouse. Most importantly, protein L does not bind to bovine Ig. Since our humanized Ab has human kappa 1 chain, we chose a protein L column to purify Hu1A4A1IgG1-furin or Hu1A4A1IgG1-2A to eliminate co-purification of bovine Ig. In this way, the purity of Hu1A4A1IgG1-furin or Hu1A4A1IgG1-2A was relatively high in SDS-PAGE as shown in FIGS. 10, 11 and 12.

When the purified product was subjected to 10% SDS-PAGE, Hu1A4A1IgG1-furin and Hu1A4A1IgG1-2A showed up in a different way. As illustrated in FIG. 12, Hu1A4A1IgG1-2A showed the same patterns as a control human IgG1, one band of ~150 kDa in non-reducing condition (intact disulfide bridges) and two bands, 50 kDa for heavy chains and 25 kDa for light chains (broken disulfide bridges) in reducing condition, indicating that the 2A linker underwent self-processing perfectly. On the other hand, Hu1A4A1IgG1-furin showed only one clear band of ~75 kDa in reducing condition observed as illustrated in FIGS. 10 and 11, indicating that the furin linker was not cleaved. However, in another study (data not shown), the same furin linker sequence was cleaved in another Fab construct expressed in a mammalian system. This indicated the conformation of expressed Hu1A4A1IgG1-furin probably rendered the furin linker inaccessible to furin or that the sequence surrounding the furin linker influenced furin cleavage.

The specific binding reactivities of purified Hu1A4A1IgG1-furin and Hu1A4A1IgG1-2A to VEEV E2 antigen were examined by ELISA. As illustrated in FIG. 13, both versions of the Hu1A4A1IgG1 were found to bind to VEEV E2 in a dose-dependent manner, similar to the binding to VEEV E2 of its parental murine 1A4A1, indicating this non-cleaved Ab was still reactive to VEEV E2 antigen in ELISA. Furthermore, both versions were evaluated for their ability to block VEEV infection in Vero cells using a standard plaque-reduction assay. The Hu1A4A1IgG1-fruin showed a neutralizing activity with 50% plaque reduction neutralization titre at 0.78 µg/ml, whereas Hu1A4A1IgG1-2A showed a much higher neutralization titre at 0.1 µg/ml.

Figure 14:
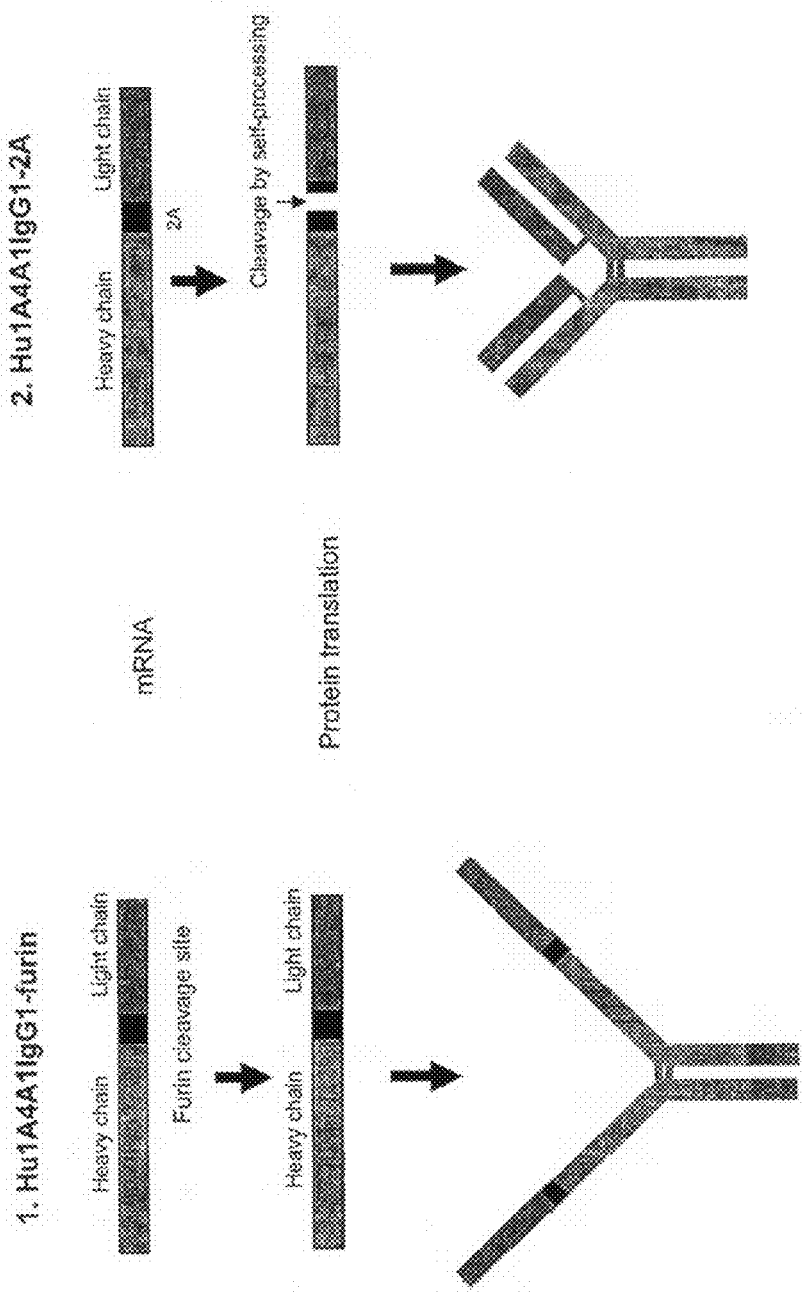
FIG. 14 schematically illustrates Hu1A4A1IgG1-2A was cleaved between the heavy and light chains as expected, whereas Hu1A4A1IgG1-furin was not cleaved.

From the above results, it is concluded that the murine 1A4A1 Ab was successfully humanized. As illustrated in FIG. 14, the expressed and purified Ab of Hu1A4A1IgG1-2A was cleaved between the heavy and light chains as expected; however, Hu1A4A1IgG1-furin was not cleaved. Nevertheless, the present inventors have exhibited that both versions of the Hu1A4A1IgG1 retained the antigen binding specificity and virus neutralizing activity. Thus, the Hu1A4A1IgG1-furin or Hu1A4A1IgG1-2A discussed and characterized herein would serve as an effective prophylactic and therapeutic agent against VEEV infection.

Example 2

In Vivo Study—Protection or Pre-Exposure Prophylaxis of Mice from VEEV Challenge by Passive Immunization with Hu1A4A1IgG1-furin or Hu1A4A1IgG1-2A Materials and Methods
Passive Immunization (Pre-Exposure Prophylaxis)
Balb/c mice aged 6-8 weeks were injected intraperitoneally (i.p) with 50 µg of Hu1A4A1IgG1-furin or Hu1A4A1IgG1-2A in 100 µl PBS, human IgG in 100 µl PBS (positive control) or 100 µl PBS alone (negative control) 24 h prior to VEEV challenge.

VEEV Challenge
Each mouse was challenged subcutaneously (s.c.) with 30-50 plaque forming units (pfu) of virulent VEEV (Trinidad donkey, TRD) in 50 µl of Leibovitz L15 maintenance medium (L15MM) 24 h after passive immunization. The challenge dose approximated to 100×50% lethal dose (LD50). Mice were examined frequently for signs of illness for 14 days, and humane endpoints were used.

Results
Hu1A4A1IgG1-furin or Hu1A4A1IgG1-2A Clearance in Mice
To determine the half-life of Hu1A4A1IgG1-furin or Hu1A4A1IgG1-2A in mouse serum, groups of 4 mice, were injected i.p. with 50 µg, each mouse, of either Hu1A4A1IgG1-furin or Hu1A4A1IgG1-2A, or human anti-VEEV IgG and bled from the vein at increasing time intervals after injection. The quantity of Ab present in serum samples was estimated by immunoassay. Hu1A4A1IgG1-furin or Hu1A4A1IgG1-2A had a similar half-life as human anti-VEEV IgG, around 10 days.

Protection of Mice from VEEV Challenge by Passive Immunization with Hu1A4A1IgG1-furin or Hu1A4A1IgG1-2A Groups of 8 mice were injected i.p. with the Hu1A4A1IgG1-furin, Hu1A4A1IgG1-2A, human IgG (positive control) or PBS alone (negative control) and 24 h later challenged s.c. with 100×LD50 of VEEV. None of the mice treated only with human IgG (positive control) or PBS alone (negative control) survived. All the Hu1A4A1IgG1-furin or Hu1A4A1IgG1-2A treated mice survived the VEEV challenge without any clinical signs at 14 days post-challenge.

Discussion
Passive immunization of the Hu1A4A1IgG1-furin or Hu1A4A1IgG1-2A in mice (50 µg/mouse) 24 h before virulent VEEV challenge provided 100% protection against 100× LD50 challenge of VEEV when mice were treated with 50 µg/each mouse of Hu1A4A1IgG1-furin or Hu1A4A1IgG1-2A. The mice were also found to be asymptomatic throughout the 14 day observation period. These results indicate that the humanized anti-VEEV rAbs of the present invention have pre-exposure prophylactic capacity against VEEV infections. The half-lives of the humanized anti-VEEV rAbs in mice was around 10 days suggesting that the humanized anti-VEEV rAbs of the invention would be an effective prophylactic against VEEV for at least several weeks. Thus, the rAbs of the invention have been demonstrated to have functionality as an immunization agent against VEEV infection.

Example 3

In Vivo Study—Treatment or Post-Exposure Therapy of Mice after VEEV Challenge by Passive Immunization with Hu1A4A1IgG1-furin or Hu1A4A1IgG1-2A Materials and Methods
Post-Exposure Therapy
Balb/c mice aged 6-8 weeks were challenged s.c. with 100×LD50 of virulent VEEV in 50 µl of L15MM per mouse. At 24 h post-challenge, mice were injected i.p with 50 µg of Hu1A4A1IgG1-furin or Hu1A4A1IgG1-2A in 100 µl PBS, or 100 µl PBS alone. Mice were examined frequently for signs of illness for 20 days, and humane endpoints were used.

Results

The half-lives of Hu1A4A1IgG1-furin or Hu1A4A1IgG1-2A was determined above in Example 2.

Treatment of Mice After VEEV Challenge Using Hu1A4A1IgG1-furin or Hu1A4A1IgG1-2A Groups of 8 mice were challenged s.c. with 100×LD50 of VEEV. Twenty-four hours later, the infected mice were administered i.p. with Hu1A4A1IgG1-furin, Hu1A4A1IgG1-2A or PBS alone (50 μg/mouse). All the Hu1A4A1IgG1-2A-treated mice survived throughout the observation period (20 days post-challenge) with minor clinical signs. All Hu1A4A1IgG1-furin or PBS-treated mice died.

Discussion

Passive immunization of the Hu1A4A1IgG1-2A in mice (50 μg/mouse) 24 h after virulent VEEV challenge provided 100% protection against 100×LD50 challenge of VEEV with only minor clinical signs, indicating the Hu1A4A1IgG1-2A has post-exposure therapeutic capacity against VEEV infections. Unfortunately, Hu1A4A1IgG1-furin did not show any post-exposure therapy capacity. One possible reason for this finding may be that the antigen binding capacity of uncut Hu1A4A1IgG1-furin is inferior to the cleaved Hu1A4A1IgG1-2A.

BIBLIOGRAPHY

One or more of the following documents have been referred to in the present disclosure. The following documents are incorporated herein by reference in their entirety.

[1] Weaver S C, Ferro C, Barrera R, Boshell J, Navarro J C. Venezuelan equine encephalitis. Annu Rev Entomol, 2004; 49:141-74.

[2] Rivas F, Diaz L A, Cardenas V M, Daza E, Bruzon L, Alcala A, et al. Epidemic Venezuelan equine encephalitis in La Guajira, Colombia, 1995. J Infect Dis, 1997; 175: 828-32.

[3] Pittman P R, Makuch R S, Mangiafico J A, Cannon T L, Gibbs P H, Peters C J. Long-term duration of detectable neutralizing antibodies after administration of live-attenuated VEE vaccine and following booster vaccination with inactivated VEE vaccine. Vaccine, 1996; 14:337-43.

[4] Jahrling P B, Stephenson E H. Protective efficacies of live attenuated and formaldehyde-inactivated Venezuelan equine encephalitis virus vaccines against aerosol challenge in hamsters. J Clin Microbiol, 1984; 19:429-31.

[5] France J K, Wyrick B C, Trent D W. Biochemical and antigenic comparison of the envelope glycoproteins of Venezuelan equine encephalomyelitis virus strains. J Gen Virol, 1979; 44:725-40.

[6] Roehrig J T, Day J W, Kinney R M. Antigenic analysis of the surface glycoproteins of a Venezuelan equine encephalomyelitis virus (TC-83) using monoclonal antibodies. Virology, 1982; 118:269-78.

[7] Roehrig J T, Mathews J H. The neutralization site on the E2 glycoprotein of Venezuelan equine encephalomyelitis (TC-83) virus is composed of multiple conformationally stable epitopes. Virology, 1985; 142:347-56.

[8] Schroff R W, Foon K A, Beatty S M, Oldham R K, Morgan Jr A C. Human anti-murine immunoglobulin responses in patients receiving monoclonal antibody therapy. Cancer Res, 1985; 45:879-85.

[9] Verhoeyen M, Milstein C, Winter G. Reshaping human antibodies: grafting an antilysozyme activity. Science, 1988; 239:1534-6.

[10] Dall'Acqua W F, Damschroder M M, Zhang J, Woods R M, Widjaja L, Yu J, et al. Antibody humanization by framework shuffling. Methods, 2005; 36:43-60.

[11] Hu W G, Alvi A Z, Fulton R E, Suresh M R, Nagata L E. Genetic engineering of streptavidin-binding peptide tagged single-chain variable fragment antibody to Venezuelan equine encephalitis virus. Hybrid Hybridomics, 2002; 21:415-20.

[12] Hwang W Y, Almagro J C, Buss T N, Tan P, Foote J. Use of human germline genes in a CDR homology-based approach to antibody humanization. Methods, 2005; 36:35-42.

[13] van den Ouweland A M, van Duijnhoven H L, Keizer G D, Dorssers L C, Van de Ven W J. Structural homology between the human fur gene product and the subtilisin-like protease encoded by yeast KEX2. Nucleic Acids Res, 1990; 18:664.

[14] Fulton R E, Nagata, L, Alvi, A; U.S. Pat. No. 6,818,748, Nov. 16, 2004.

[15] Johnson K M, Martin D H. Venezuelan equine encephalitis. Adv. Vet Sci Comp Med. 1974; 18(0):79-116.

[16] Groot H, The health and economic importance of Venezuelan equine encephalitis (VEE) in Venezuelan encephalitis, Scientific publication no. 243, 1972, pp. 7-16, Pan American Health Organization, Washington D.C.

[17] Phillpotts R J, Jones L D, Howard S C, Monoclonal antibody protects mice against infection and disease when given either before or up to 24 h after airborne challenge with virulent Venezuelan equine encephalitis virus. Vaccine, 2002 Feb. 22; 20 (11-12): 1497-504.

[18] Hu W G, Chau D, Wu J, Jager S, Nagata L, Humanization and mammalian expression of murine monoclonal antibody against Venezuelan equine encephalitis virus. Vaccine, 2007; 25:3210-3214.

Although the invention has been described with reference to certain specific embodiments, various modifications thereof will be apparent to those skilled in the art without departing from the purpose and scope of the invention as outlined in the claims appended hereto. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference in their entirety.

We claim:

1. A method of inhibiting Venezuelan equine encephalitis virus (VEEV) infection in a human, the method comprising administering to said human a humanized recombinant antibody comprising a human Ig framework and having grafted thereon complementarity determining regions, CDRs, from the murine monoclonal antibody 1A4A1, wherein:
   the antibody is capable of inhibiting VEEV infection when administered prior to or after VEEV exposure; and,
   the antibody is encoded by the nucleic acid sequence according to SEQ ID NO: 13.

2. The method according to claim 1 wherein said antibody VH region has the amino acid sequence according to SEQ ID NO: 7.

3. The method according to claim 1 wherein said antibody VL region has the amino acid sequence according to SEQ ID NO: 8.

4. The method according to claim 1 wherein said antibody has the amino acid sequence according to SEQ ID NO: 14.

5. The method according to claim 1 wherein said antibody is encoded by an expression vector.

6. The method according to claim 1 wherein said antibody is expressed by an isolated transformed host cell.

7. The method according to claim 1 wherein the antibody is administered to the human at least 24 hours prior exposure to VEEV.

8. A method of passive transfer of immunity, to a human, against Venezuelan equine encephalitis virus (VEEV) infection, after exposure to VEEV, the method comprising administering to said human a humanized recombinant antibody comprising a human Ig framework and having grafted thereon complementarity determining regions, CDRs, from the murine monoclonal antibody 1A4A1, wherein the antibody is encoded by the nucleic acid sequence according to SEQ ID NO: 13.

9. The method according to claim 8 wherein the antibody is administered to the human within 24 hours after exposure to VEEV.

10. The method according to claim 8 wherein the antibody has the amino acid sequence according to SEQ ID NO: 14.

* * * * *